(12) United States Patent
Chou

(10) Patent No.: US 11,535,870 B2
(45) Date of Patent: Dec. 27, 2022

(54) ADENO-ASSOCIATED VIRUS VECTORS ENCODING MODIFIED G6PC AND USES THEREOF

(71) Applicant: The U.S.A., as represented by the Secretary, Department of Health and Human Services, Bethesda, MD (US)

(72) Inventor: Janice J. Chou, North Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 619 days.

(21) Appl. No.: 16/526,327

(22) Filed: Jul. 30, 2019

(65) Prior Publication Data
US 2019/0345502 A1    Nov. 14, 2019

Related U.S. Application Data

(62) Division of application No. 15/538,852, filed as application No. PCT/US2015/067338 on Dec. 22, 2015, now Pat. No. 10,415,044.

(60) Provisional application No. 62/096,400, filed on Dec. 23, 2014.

(51) Int. Cl.

| | |
|---|---|
| *A61K 48/00* | (2006.01) |
| *C12N 15/864* | (2006.01) |
| *C12N 15/85* | (2006.01) |
| *C12N 9/16* | (2006.01) |
| *A61K 38/00* | (2006.01) |
| *A61K 38/47* | (2006.01) |
| *C12N 15/66* | (2006.01) |
| *A61K 45/06* | (2006.01) |

(52) U.S. Cl.
CPC .......... *C12N 15/8645* (2013.01); *A61K 38/00* (2013.01); *A61K 38/47* (2013.01); *A61K 48/00* (2013.01); *C12N 9/16* (2013.01); *C12N 15/66* (2013.01); *C12N 15/85* (2013.01); *C12Y 301/03009* (2013.01); *A61K 45/06* (2013.01); *C12Y 302/00* (2013.01)

(58) Field of Classification Search
None
See application file for complete search history.

(56) References Cited

U.S. PATENT DOCUMENTS 9,644,216 B2    5/2017    Chou et al.

FOREIGN PATENT DOCUMENTS

| EP | 2 412 387 | 2/2012 |
|---|---|---|
| WO | WO 01/92497 | 12/2001 |

OTHER PUBLICATIONS

Crane et al., "Rescue administration of a helper-dependent adenovirus vector with long-term efficacy in dogs with glycogen storage disease type 1a," *Gene Ther.*, vol. 19:443-452, 2012.
Wang, "Adeno-Associated Virus Gene Therapy Prevents Hepatocellular Adenoma in Murine Model of Glycogen Storage Disease Type 1a," *Hepatology*, vol. 56:1593-1595, 2012.
Brooks et al., "Pathogenesis of Growth Failure and Partial Reversal with Gene Therapy in Murine and Canine Glycogen Storage Disease Type Ia," *Mol. Genet. Metab.*, vol. 109:161-170, 2013.
Chou et al., "Type I Glycogen Storage Diseases: Disorders of the Glucose-6-Phosphatase Complex,"*Curr. Mol. Med.*, vol. 2:121-143, 2002.
Chou et al., "Glycogen Storage Disease Type I and G6Pase-β deficiency: Etiology and Therapy," *Nat. Rev. Endocrinol.* vol. 6(12):676-688, 2010.
Chou and Mansfield, "Recombinant AAV-Directed Gene Therapy for Type I Glycogen Storage Diseases," *Expert Opin. Biol. Ther.*, vol. 11:1011-1024, 2011.
Daya and Berns, "Gene Therapy Using Adeno-Associated Virus Vectors," *Clin. Microbiol. Rev.*, vol. 21:583-593, 2008.
GenBank Accession No. NG_011808.1, deposited Apr. 10, 2009 (8 pages).
Ghosh et al., "Long-Term Correction of Murine Glycogen Storage Disease Type Ia by Recombinant Adeno-Associated Vims-1-Mediated Gene Transfer," *Gene Ther.*, vol. 13:321-329, 2006.
Grieger et al., "Packaging Capacity of Adeno-Associated Virus Serotypes: Impact of Larger Genomes on Infectivity and Postentry Steps," *J. Virol.*, vol. 79:9933-9944, 2005.
Huston et al., "Correction of Murine SCID-X1 by Lentiviral Gene Therapy Using a Codon-Optimized IL2RG Gene and Minimal Pretransplant Conditioning," *Mol. Ther.*, vol. 19:1867-1877, 2011.
Koeberl et al., "AAV Vector—Mediated Reversal of Hypoglycemia in Canine and Murine Glycogen Storage Disease Type Ia," *Mol. Ther.*, vol. 16:665-672, 2008.
Lee et al., "Prevention of Hepatocellular Adenoma and Correction of Metabolic Abnormalities in Murine Glycogen Storage Disease Type Ia by Gene Therapy," *Hepatol.*, vol. 56:1719-1729, 2012.
Lee et al., "The Upstream Enhancer Elements of the G6PC Promoter are Critical for Optimal G6PC Expression in Murine Glycogen Storage Disease Type Ia," *Mol. Genet. Metab.*, vol. 110:275-280, 2013.

(Continued)

*Primary Examiner* — Marcia S Noble
(74) *Attorney, Agent, or Firm* — Klarquist Sparkman, LLP

(57) ABSTRACT

Modified G6PC (glucose-6-phosphatase, catalytic subunit) nucleic acids and glucose-6-phosphatase-α (G6Pase-α) enzymes with increased phosphohydrolase activity are described. Also described are vectors, such as adeno-associated virus (AAV) vectors, and recombinant AAV expressing modified G6Pase-α. The disclosed AAV vectors and rAAV can be used for gene therapy applications in the treatment of glycogen storage disease, particularly glycogen storage disease type Ia (GSD-Ia), and complications thereof.

10 Claims, 7 Drawing Sheets

Specification includes a Sequence Listing.

(56) References Cited

OTHER PUBLICATIONS

Weinstein et al., "Adeno-Associated Virus-Mediated Correction of a Canine Model of Glycogen Storage Disease Type Ia," *Hum. Gene Ther.*, vol. 21:903-910, 2010.

Wu et al., "Optimization of Self-Complementary AAV Vectors for Liver-Directed Expression Results in Sustained Correction of Hemophilia B at Low Vector Dose," *Mol. Ther.*, vol. 16:280-289, 2008.

Yiu et al., "Complete Normalization of Hepatic G6PC Deficiency in Murine Glycogen Storage Disease Type Ia Using Gene Therapy," *Mol. Ther.*, vol. 18:1076-1084, 2010.

GenBank Accession No. NM_001002993.1, Feb. 23, 2014 (3 pages).

E3K: GAA-AAA (nt 7-9)
ATGGAG[GAA]G GAATGAATGT TCTCCATGAC TTTGGGATCC AGTCAACACA TTACCTCCAG    G6PC--60

GTGAATTACC AAGACTCCCA GGACTGGTTC ATCTTGGTGT CCGTGATCGC AGACCTCAGG    G6PC--120

Q54R: CAG-CGT (nt 160-162)
AATGCCTTCT ACGTCCTCTT CCCCATCTGG TTCCATCT[C AG]GAAGCTGT GGGCATTAAA    G6PC--180

CTCCTTTGGG TAGCTGTGAT TGGAGACTGG CTCAACCTCG TCTTTAAGTG GATTCTCTTT    G6PC--240

GGACAGCGTC CATACTGGTG GGTTTTGGAT ACTGACTACT ACAGCAACAC TTCCGTGCCC    G6PC--300

CTGATAAAGC AGTTCCCTGT AACCTGTGAG ACTGGACCAG GGAGCCCCTC TGGCCATGCC    G6PC-360

Q139R: CAG-CGG (nt 415-417)
ATGGGCACAG CAGGTGTATA CTACGTGATG GTCACATCTA CTCTTTCCAT CTTT[CAG]GGA    G6PC-420

I142K: ATA-AAA (nt 424-426)
AAG[ATA]AAGC CGACCTACAG ATTCGGTGC TTGAATGTCA TTTTGTGGTT GGGATTCTGG    G6PC--480

GCTGTGCAGC TGAATGTCTG TCTGTCACGA ATCTACCTTG CTGCTCATTT CCTCATCAA    G6PC--540

S196R: AGC-CGC (nt (586-588) H199Q: CAC-CAG (nt 595-597)
GTTGTTGCTG GAGTCCTGTC A[GC]CATTGCT GTTCAGAAA CTTT[CA]C CATC[CA]CAGC    G6PC--600

ATCTATAATG CCAGCCTCAA GAAATATTTT CTCATTACCT TCTTCCTGTT CAGCTTCGCC    G6PC--660

ATCGGATTTT ATCTGCTGCT CAAGGGACTG GGTGTAGACC TCCTGTGGAC TCTGGAGAAA    G6PC--720

Q242R: CAG-AGG (nt 724-726); Q247R: CAG-CCG (nt 739-741)
GCC[CAG]AGT GGTGCGAC[CA G]CAGAATGG GTCCACATTG ACACCACACC TTTGCCAGC    G6PC--780

CTCCTCAAGA ACCTGGGCAC GCTCTTTGGC CTGGGGCTGG CTCTCAACTC CAGCATGTAC    G6PC-840

L292F: CTC-TTC (nt 874-876); S298C:TCT-TGC (nt 892-894)
AGGGAGAGCT GCAAGGGGAA ACTCAGCAAG TGG[CT]CCAT TCCGCCTCAG C[TC]ATTGTA    G6PC-900

A301V: GCC-GTC (nt 901-903)       V318T: GTC-ACT (nt 952-954)
[GC]TCCCTCG TCCTCCTGCA CGTCTTTGAC TCCTTGAAAC CCCCATCCCA A[GT]GAGCTG    G6PC-960

V324T: GTC-ACC (nt 970-972); V332A (GTA-GCA) (nt 994-996)
GTCTTCTAC[G T]GTGTCCTT CTGCAAGAGT GCC[GTA]GTGC CCTGGCATC CGTCAGTGTC    G6PC-1020

Q347R: CAG-CGG; L349F: CTG-TTC; G350D: GGC-GAC; H353D: CAC-GAC
ATCCCCTACT GCCTCGCC[CA G]GTC[TGGG]C CAGCC[CAG]A AGAAGTCGTT GTAA    G6PC-1074
(SEQ ID NO: 11)

Q347R: CAG-CGG (nt 1039-1041)
L349F: CTG-TTC (nt 1045-1047)
G350D: GGC-GAC (nt 1048-1050)
H353D: CAC-GAC (nt 1057-1059)

ADENO-ASSOCIATED VIRUS VECTORS ENCODING MODIFIED G6PC AND USES THEREOF

CROSS REFERENCE TO RELATED APPLICATIONS

This application is a divisional of U.S. application Ser. No. 15/538,852, filed Jun. 22, 2017, issued as U.S. Pat. No. 10,415,044 on Sep. 17, 2019, which is the U.S. National Stage of International Application No. PCT/2015/067338, filed Dec. 22, 2015, published in English under PCT Article 21(2), which claims the benefit of U.S. Provisional Application No. 62/096,400, filed Dec. 23, 2014. The above-listed applications are herein incorporated by reference in their entirety.

FIELD

This disclosure concerns gene therapy vectors encoding a modified glucose-6-phosphatase-α (G6PC) enzyme with increased activity and its use, such as for the treatment of glycogen storage disease (GSD) and complications associated with GSD.

BACKGROUND

Glycogen storage disease type Ia (GSD-Ia or von Gierke disease, MIM232200) is caused by a deficiency in glucose-6-phosphatase-α (G6Pase-α or G6PC), an enzyme that is expressed primarily in the liver, kidney, and intestine (Chou et al., *Nat Rev Endocrinol* 6:676-688, 2010). G6Pase-α, encoded by the G6PC gene, is a hydrophobic protein anchored in the endoplasmic reticulum (ER) by nine transmembrane helices (Chou et al., *Nat Rev Endocrinol* 6:676-688, 2010). This enzyme catalyzes the hydrolysis of glucose-6-phosphate (G6P) to glucose and phosphate in the terminal step of glycogenolysis and gluconeogenesis. Patients affected by GSD-Ia are unable to maintain glucose homeostasis and present with fasting hypoglycemia, growth retardation, hepatomegaly, nephromegaly, hyperlipidemia, hyperuricemia, and lactic academia (Chou et al., *Nat Rev Endocrinol* 6:676-688, 2010).

There is currently no cure for GSD-Ia. Hypoglycemia can be managed using dietary therapies (Greene et al., *N Engl J Med* 294:423-425, 1976; Chen et al., *N Engl J Med* 310:171-175, 1984) that enable patients to attain near normal growth and pubertal development. However, the longer term clinical complications, and their underlying pathological processes, remain uncorrected. One of the most significant chronic risks is hepatocellular adenoma (HCA), that develops in 70-80% of GSD-I patients over 25 years old (Chou et al., *Nat Rev Endocrinol* 6:676-688, 2010; Labrune et al., *J Pediatr Gastroenterol Nutr* 24:276-279, 1997; Rake et al., *Eur J Pediatr* 161(Suppl 1):S20-S34, 2002). HCAs in GSD-Ia patients are small, multiple, and nonencapsulated, with complications including local compression and intratumoral hemorrhage. In 10% of GSD-Ia patients, HCAs undergo malignant transformation to hepatocellular carcinoma (HCC) (Chou et al., *Nat Rev Endocrinol* 6:676-688, 2010; Rake et al., *Eur J Pediatr* 161(Suppl 1):S20-S34, 2002; Franco et al., *J Inherit Metab Dis* 28:153-162, 2005).

Although gene therapy studies using recombinant adeno-associated virus (AAV) carrying G6Pase-α have previously been performed in animal models of GSD-Ia, none have been capable of completely correcting hepatic G6Pase-α deficiency. Thus, a need exists for an improved gene therapy vector for the treatment of GSD-Ia and its associated complications.

SUMMARY

It is disclosed herein that the canine G6Pase-α enzyme is more active than the human G6Pase-α enzyme. An amino acid sequence alignment of the two proteins revealed that they differ primarily at 18 residues. To identify human G6Pase-α mutants with increased phosphohydrolase activity, mutants were generated that contain one or two corresponding amino acids from canine G6Pase-α.

Provided herein are isolated nucleic acid molecules encoding a modified G6Pase-α. In some embodiments, the modified G6Pase-α comprises a serine to cysteine substitution at amino acid 298 of human G6Pase-α, such as the modified G6Pase-α of SEQ ID NO: 8. In some examples, the nucleic acid molecules comprise the nucleotide sequence of SEQ ID NO: 6 or SEQ ID NO: 7.

Further provided are vectors, such as adeno-associated virus (AAV) vectors, that include the disclosed nucleic acid molecules encoding modified human G6Pase-α. In some examples, the vectors further comprise a promoter, such as a human G6PC promoter/enhancer (GPE).

Also provided are recombinant AAV (rAAV) comprising the nucleic acid molecules encoding modified human G6Pase-α. Further provided are isolated host cells comprising the nucleic acid molecules or vectors disclosed herein. For example, the isolated host cells can be cells suitable for propagation of rAAV.

Compositions comprising the disclosed nucleic acid molecules, vectors and rAAV are further provided by the present disclosure.

Further provided is a method of treating a subject diagnosed with a glycogen storage disease. In some embodiments, the method includes selecting a subject with glycogen storage disease type Ia (GSD-Ia) and administering to the subject a therapeutically effective amount of the rAAV, or compositions comprising the rAAV, disclosed herein.

Also provided is a method of promoting glucose homeostasis; inhibiting hypoglycemia; inhibiting or preventing the development of HCA; inhibiting or preventing the development of HCC; inhibiting or preventing renal dysfunction or failure; or treating any other complication associated with GSD-Ia, in a subject with a deficiency in G6Pase-α by administering to the subject a therapeutically effective amount of the rAAV, or compositions comprising the rAAV, disclosed herein.

The foregoing and other objects, features, and advantages of the invention will become more apparent from the following detailed description, which proceeds with reference to the accompanying figures.

BRIEF DESCRIPTION OF THE DRAWINGS

FIG. 1 is an alignment of the canine (SEQ ID NO: 1) and human (SEQ ID NO: 2) G6Pase-α protein sequences. The 18 amino acid residues that differ between the canine and human sequences are indicated by arrows.

FIG. 4 shows the nucleotide sequence of the G6PC cDNA (SEQ ID NO: 11), with the location of each of the 18 human G6PC mutants indicated. For site-directed mutagenesis, 20-nucleotide sense and antisense primers were designed such that the codon to be mutated was located in the middle of each primer.

FIG. 6A is a graph showing hepatic G6Pase-α activity in control (n=7), L-G6pc$^{-/-}$ (n=7) and AAV mice (n=8). FIG. 6B shows images of representative H&E-stained livers of control, L-G6pc$^{-/-}$ and AAV mice. FIG. 6C is a graph showing fasting glucose tolerance (FGT) of control (n=13), L-G6pc$^{-/-}$ (n=6) and AAV mice (n=8). FIG. 6D is a graph showing liver weights of control, L-G6pc$^{-/-}$ and AAV mice (n=8). FIG. 6E is a graph showing hepatic contents of glycogen and triglyceride of control, L-G6pc$^{-/-}$ and AAV mice (n=8). Data represent the mean±SEM. *P<0.05, **P<0.005.

SEQUENCE LISTING

Figure 2:
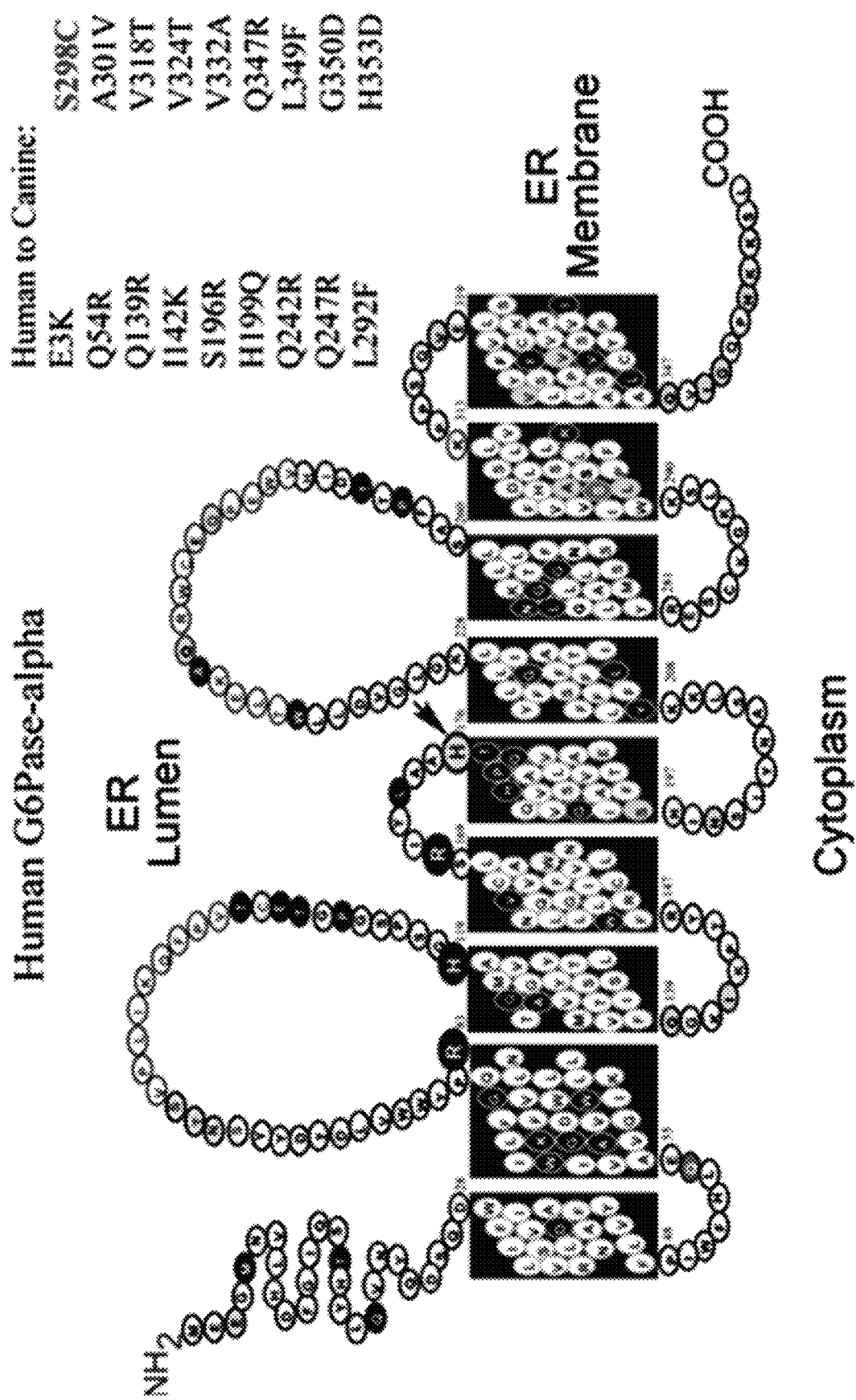
FIG. 2 depicts human G6Pase-α, which is anchored into the endoplasmic reticulum membrane by 9 helices, H1 to H9 (Pan et al *J Biol Chem* 273:6144-6148, 1998). The amino acid differences between human and canine G6Pase-α are listed.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 17, 2019, 52.9 KB, which is incorporated by reference herein. In the accompanying Sequence Listing:

SEQ ID NO: 1 is the amino acid sequence of canine G6Pase-α protein.

SEQ ID NO: 2 is the amino acid sequence of human G6Pase-α protein.

SEQ ID NO: 3 is the nucleotide sequence of pTR-GPE-human G6PC having the following features:
  ITR—nucleotides 17-163
  G6PC promoter/enhancer—nucleotides 182-3045
  Stuffer—nucleotides 3051-3184
  Intron—nucleotides 3185-3321
  Stuffer—nucleotides 3322-3367
  G6PC coding sequence—nucleotides 3368-4441
  ITR—nucleotides 4674-4819.

SEQ ID NO: 4 is the nucleotide sequence of pTR-GPE-human G6PC-S298C having the following features:
  ITR—nucleotides 17-163
  G6PC promoter/enhancer—nucleotides 182-3045
  Stuffer—nucleotides 3051-3184
  Intron—nucleotides 3185-3321
  Stuffer—nucleotides 3322-3367
  G6PC coding sequence—nucleotides 3368-4441
  S298C mutation—nucleotides 4259-4261 (TCT to TGC)
  ITR—nucleotides 4674-4819.

SEQ ID NO: 5 is the nucleotide sequence of pTR-GPE-codon optimized (co) G6PC-S298C having the following features:
  ITR—nucleotides 17-163
  G6PC promoter/enhancer—nucleotides 182-3045
  Stuffer—nucleotides 3051-3184
  Intron—nucleotides 3185-3321
  Stuffer—nucleotides 3322-3367
  Codon-optimized G6PC coding sequence—nucleotides 3368-4441
  S298C mutation—nucleotides 4259-4261 (AGC to TGC)
  ITR—nucleotides 4674-4819.

SEQ ID NO: 6 is the nucleotide sequence of a modified human G6PC encoding S298C G6Pase-α.

SEQ ID NO: 7 is the nucleotide sequence of a codon-optimized, modified human G6PC encoding S298C G6Pase-α.

SEQ ID NO: 8 is the amino acid sequence of modified human S298C G6Pase-α.

SEQ ID NO: 9 is the amino acid sequence of modified human S298C/A301V G6Pase-α.

SEQ ID NO: 10 is an amino acid consensus sequence based on alignment of human and canine G6Pase-α.

SEQ ID NO: 11 is the nucleotide sequence of the human G6PC coding region.

DETAILED DESCRIPTION

I. Abbreviations

AAV adeno-associated virus
CBA chicken β-actin
CMV cytomegalovirus
co codon optimized
FGT fasting glucose tolerance
G6P glucose-6-phosphate
G6Pase-α glucose-6-phosphatase-α
G6PC glucose-6-phosphatase, catalytic subunit
G6PT glucose-6-phosphate transporter
GPE G6PC promoter/enhancer
GSD glycogen storage disease
HCA hepatocellular adenoma
HCC hepatocellular carcinoma
ITR inverted terminal repeat
ORF open reading frame
rAAV recombinant AAV
SEM standard error of the mean
vg viral genomes
vp viral particles
WT wild type II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

Administration/Administer: To provide or give a subject an agent, such as a therapeutic agent (e.g. a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Enhancer: A nucleic acid sequence that increases the rate of transcription by increasing the activity of a promoter.

G6PC: A gene located on human chromosome 17q21 that encodes glucose-6-phosphatase-α (G6Pase-α). G6Pase-α is a 357 amino acid hydrophobic protein having 9 helices that anchor it in the endoplasmic reticulum (Chou et al., *Nat Rev Endocrinol* 6:676-688, 2010). G6Pase-α is depicted in FIG. 2. The G6Pase-α protein catalyzes the hydrolysis of glucose 6-phosphate to glucose and phosphate in the terminal step of gluconeogenesis and glycogenolysis and is a key enzyme in glucose homeostasis. Deleterious mutations in the G6PC gene cause glycogen storage disease type Ia (GSD-Ia), which is a metabolic disorder characterized by severe fasting hypoglycemia associated with the accumulation of glycogen and fat in the liver and kidneys.

Glycogen storage disease (GSD): A group of diseases that result from defects in the processing of glycogen synthesis or breakdown within muscles, liver and other tissues. GSD can either be genetic or acquired. Genetic GSD is caused by any inborn error of metabolism involved in these processes. There are currently 11 recognized glycogen storage diseases (GSD type I, II, III, IV, V, VI, VII, IX, XI, XII and XIII). GSD-I consists of two autosomal recessive disorders, GSD-Ia and GSD-Ib (Chou et al., *Nat Rev Endocrinol* 6:676-688, 2010). GSD-Ia results from a deficiency in glucose-6-phosphatase-α. Deficiencies in the glucose-6-phosphate transporter (G6PT) are responsible for GSD-Ib.

Glycogen storage disease type Ia (GSD-Ia): Also known as von Gierke disease, GSD-Ia is the most common glycogen storage disease, having an incidence of about 1 in 100,000 live births. GSD-Ia is a genetic disease resulting from deficiency of the enzyme glucose-6-phosphatase-α (G6Pase-α). Deficiency in G6Pase-α impairs the ability of the liver to produce free glucose from glycogen and from gluconeogenesis. Patients affected by GSD-Ia are unable to maintain glucose homeostasis and present with fasting hypoglycemia, growth retardation, hepatomegaly, nephromegaly, hyperlipidemia, hyperuricemia, and lactic academia (Chou et al., *Nat Rev Endocrinol* 6:676-688, 2010). There is currently no cure for GSD-Ia.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are essential cis components for generating AAV integrating vectors.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Modified: In the context of the present disclosure, a "modified" G6PC or G6Pase-α refers to a G6PC nucleic acid sequence or a G6Pase-α amino acid sequence that comprises at least one nucleic acid or amino acid substitution, deletion or insertion compared to the wild type sequence (such as compared to the human G6PC coding sequence set forth as nucleotides 3368-4441 of SEQ ID NO: 3, or relative to the human G6Pase-α amino acid sequence set forth as SEQ ID NO: 2).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as GSD-Ia) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule (such as a recombinant nucleic acid molecule encoding G6Pase-α) has been packaged.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Stuffer sequence: Refers to a sequence of nucleotides contained within a larger nucleic acid molecule (such as a vector) that is typically used to create desired spacing between two nucleic acid features (such as between a promoter and a coding sequence), or to extend a nucleic acid molecule so that it is of a desired length. Stuffer sequences do not contain protein coding information and can be of unknown/synthetic origin and/or unrelated to other nucleic acid sequences within a larger nucleic acid molecule.

Subject: Living multi-cellular vertebrate organisms, a category that includes human and non-human mammals.

Synthetic: Produced by artificial means in a laboratory, for example a synthetic nucleic acid can be chemically synthesized in a laboratory.

Therapeutically effective amount: A quantity of a specified pharmaceutical or therapeutic agent (e.g. a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Glycogen storage disease type Ia (GSD-Ia) is an inherited disorder of metabolism associated with life-threatening hypoglycemia, hepatic malignancy, and renal failure caused by the deficiency of glucose-6-phosphatase-α (G6Pase-α or G6PC), and primarily affecting the liver and kidney. Current therapy fails to prevent long-term complications in many patients, including growth failure, gout, pulmonary hypertension, renal dysfunction with risk for renal failure, osteoporosis, and hepatocellular adenomas (HCA) that can undergo malignant transformation to hepatocellular carcinoma (Chou et al., Curr Mol Med 2:121-143, 2002; Chou et al., Nat Rev Endocrinol 6:676-688, 2010). Therefore, the development of new therapies, such as gene therapies, is justified as a potentially curative treatment for GSD-Ia (Chou et al., Expert Opin Biol Ther 11:1011-1024, 2011).

Recombinant AAV (rAAV) vectors encoding functional G6Pase-α have been described (reviewed in Chou and Mansfield, Expert Opin Biol Ther 11:1011-1024, 2011). Previous studies using the mouse model of GSD-Ia have shown that recombinant AAV expressing G6Pase-α directed by the CBA promoter/CMV enhancer (Ghosh et al., Gene Ther 13:321-329, 2006), the canine G6PC promoter (Koeberl et al., Gene Ther 13:1281-1289, 2006), or the human G6PC promoter at nucleotides −298 to +128 of the G6PC 5' flanking region (Koeberl et al., Mol Ther 16:665-672, 2008) deliver the G6Pase-α transgene to the liver and achieve extended correction of this disorder. However, while these studies have shown promise, none have been capable of completely correcting hepatic G6Pase-α deficiency.

An example of one prior study is described by Koeberl et al. (Mol Ther 16:665-672, 2008) who developed a double-stranded, rAAV vector (rAAV-G6Pase) that was capable of treating GSD-Ia mice and GSD-Ia dogs. In addition, Yiu et al. (Mol Ther 18:1076-1084, 2010) and Lee et al. (Hepatology 56:1719-1729, 2012) describe the development of a similarly efficacious, single-stranded rAAV vector, rAAV-GPE-G6PC. The two vectors differ in several respects. First, rAAV-GPE-G6PC is a single-stranded rAAV vector while rAAV-G6Pase is a double-stranded rAAV vector. The double-stranded rAAV vector was developed to circumvent the rate-limiting step in the life cycle of AAV by converting single-stranded DNA genome into double-stranded DNA genome (Chou et al., Expert Opin Biol Ther 11:1011-1024, 2011). Second, the expression of G6Pase-α in rAAV-G6Pase is directed by the human G6PC minimal promoter/enhancer at nucleotides −382 to −1 (Koeberl et al., Mol Ther 16:665-672, 2008). The expression of G6Pase-α in rAAV-GPE-G6PC is directed by the human G6PC promoter/enhancer at nucleotides −2864 to −1 (GPE) (Yiu et al., Mol Ther 18:1076-1084, 2010; Lee et al., Hepatology 56:1719-1729, 2012). Third, the rAAV-GPE-G6PC vector contains an intron that is absent from the rAAV-G6Pase vector. Both vectors efficiently delivered the G6Pase-α transgene to the liver and corrected murine GSD-Ia (Koeberl et al., Mol Ther 16:665-672, 2008; Yiu et al., Mol Ther 18:1076-1084, 2010; Lee et al., Hepatology 56:1719-1729, 2012).

A comparative study was performed to determine which vector, rAAV-G6Pase or rAAV-GPE-G6PC, was more efficacious in treating GSD-Ia. The results showed unequivocally that the rAAV-GPE-G6PC vector was more efficient than the rAAV-G6Pase vector in correcting murine GSD-Ia. It was determined that the enhancer elements upstream of the G6PC minimal promoter were required for efficient hepatic transgene expression (Lee et al., Mol Genet Metab 10:275-280, 2013). Additional studies were carried out to determine whether the intron contained within the rAAV-GPE-G6PC vector played a role in directing hepatic G6Pase-α expression. A double-stranded rAAV vector (referred to as rAAV-miGPE-G6PC) expressing human G6Pase-α directed by the human G6PC minimal promoter at nucleotides −382 to −1, and containing the intron present in the rAAV-GPE-G6PC vector, was generated. The results showed that the rAAV-GPE-G6PC vector was more efficient than the rAAV-miGPE-G6PC vector in treating murine GSD-Ia, supporting the conclusion that the enhancer elements upstream the G6PC minimal promoter are required for efficient hepatic transgene expression (Lee et al., Mol Genet Metab 10:275-280, 2013).

Recombinant AAV vectors comprising a G6PC promoter/enhancer (GPE) element are further described in PCT Publication No. WO 2015/081101, which is herein incorporated by reference. The recombinant vectors include a GPE, a synthetic intron, and the G6PC coding region. The G6PC coding region is optionally codon-optimized for expression in human cells. The recombinant vectors further include stuffer nucleic acid sequence situated between the G6PC promoter/enhancer and the intron, as well as between the intron and the G6PC coding sequence; and 5' and 3' inverted terminal repeat (ITR) sequences.

It is disclosed in PCT Publication No. WO 2015/081101 that a G6Pase-α expressing recombinant AAV with the G6PC promoter/enhancer (rAAV-GPE-G6PC) is significantly more efficient in directing in vivo hepatic transgene expression than another G6Pase-α expressing recombinant AAV having an alternative promoter/enhancer (i.e. the chicken β-actin promoter/CMV enhancer). Over a 24-week study period, G6PC-deficient mice (a model for GSD-Ia) treated with rAAV-GPE-G6PC exhibited complete normalization of hepatic G6PC deficiency as evidenced by normal levels of blood glucose, blood metabolites, hepatic glycogen and hepatic fat (see also Yiu et al., Mol Ther 18:1076-1084, 2010). Furthermore, a longer-term study of rAAV-GPE-G6PC-treated G6pc$^{-/-}$ mice demonstrated that gene therapy mediated by rAAV-GPE-G6PC was efficacious for at least 70-90 weeks in mice expressing more than 3% hepatic G6Pase-α. In particular, rAAV-GPE-G6PC-treated mice exhibited normal hepatic fat storage, normal blood metabolite and glucose tolerance profiles, reduced fasting blood insulin levels, and had no evidence of hepatic abnormalities, such as hepatocellular adenoma (see also Lee et al., Hepatology 56:1719-1729, 2012).

Further disclosed in PCT Publication No. WO 2015/081101 was the finding that the upstream enhancer elements of the G6PC promoter are critical for optimal G6PC expression in an animal model of GSD-Ia. Specifically, it was demonstrated that treatment with rAAV-GPE-G6PC, which comprises the G6PC promoter/enhancer at nucleotides −2684 to −1 (relative to the G6PC start site) produces significantly higher levels of hepatic G6Pase-α expression, achieved greater reduction in hepatic glycogen accumulation, and led to a better toleration of fasting in a mouse model of GSD-Ia, compared to a G6Pase-α expressing recombinant AAV containing only a 383 bp minimal G6PC promoter/enhancer (see also Lee et al., Mol Genet Metab. 110(3):275-280, 2013).

Also disclosed in PCT Publication No. WO 2015/081101 was the finding that stuffer nucleotide sequences present between the G6PC promoter/enhancer and the intron, as well as between the intron and the G6PC coding sequence, are important for liver transduction and expression of G6Pase-α. In particular, recombinant AAV produced from plasmid UF11-K29-G6PC, which lacks the stuffer sequences, exhibited G6Pase activity of 7.3 nmol/min/mg. In comparison, recombinant AAV produced from plasmid UF11-GPE-G6PC, exhibited G6Pase activity of 33.0 nmol/min/mg.

In addition, data disclosed in PCT Publication No. WO 2015/081101 demonstrated that codon-optimization of the G6PC coding sequence increased efficiency of translation approximately 1.5- to 2.5-fold, resulting in significantly greater G6Pase-α expression in the liver following administration of rAAV-co-GPE-G6PC (containing a codon-optimized G6PC nucleic acid sequence), compared with administration of rAAV-GPE-G6PC, which encodes wild-type G6PC.

Thus, recombinant AAV comprising the G6PC promoter/enhancer at nucleotides −2684 to −1, a synthetic intron, stuffer sequences flanking the intron, and the G6PC coding region (wild-type or codon-optimized) are important features for efficient hepatic transgene expression and treatment of GSD-Ia in vivo.

The present disclosure shows for the first time that the human G6PC can be modified at specific positions to enhance phosphohydrolase activity of the encoded G6Pase-α enzyme. The modified G6Pase-α coding sequences can be incorporated into rAAV gene therapy vectors to enhance efficacy in the treatment of glycogen storage disease.

IV. Overview of Several Embodiments

It is disclosed herein that the canine G6Pase-α enzyme is more active than the human G6Pase-α enzyme. An amino acid alignment of the two proteins revealed that they differ in sequence at 18 residues. To identify human G6Pase-α mutants with increased phosphohydrolase activity, mutants were generated that contain at least one corresponding amino acid from canine G6Pase-α.

Provided herein are recombinant nucleic acid molecules, AAV vectors and recombinant AAV that can be used in gene therapy applications for the treatment of glycogen storage disease, specifically GSD-Ia.

Figure 1:
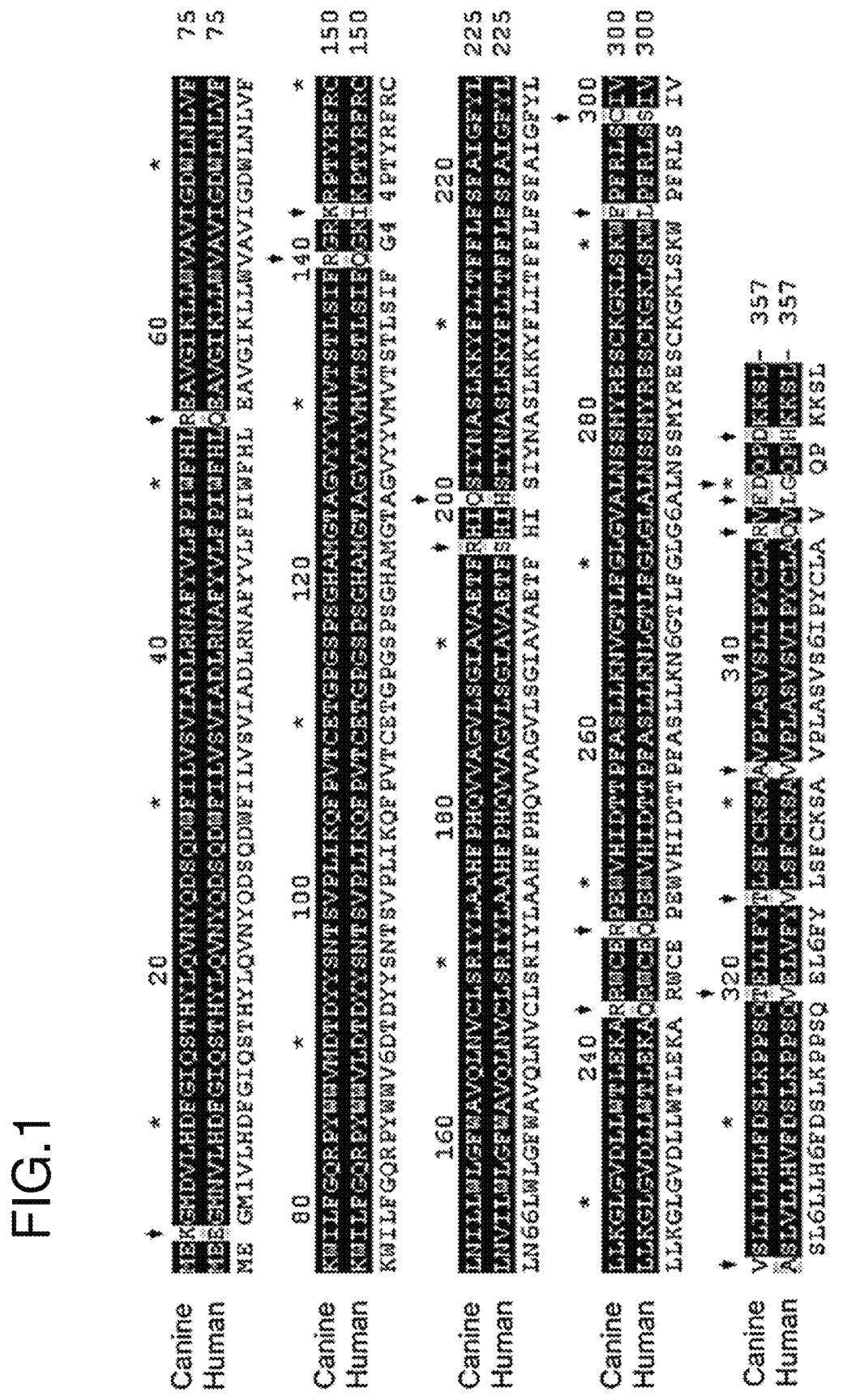

In some embodiments, provided is an isolated nucleic acid molecule encoding a modified G6Pase-α, wherein the modified G6Pase-α comprises a serine to cysteine substitution at amino acid 298 of human G6Pase-α (the amino acid sequence of wild type human G6Pase-α is set forth herein as SEQ ID NO: 2). The modified G6Pase-α can include modifications at additional residues so long as the protein retains enzymatic activity. For example, the modified G6Pase-α can include substitutions at other residues that differ between the canine and human G6Pase-α sequences, such residues include positions 3, 54, 139, 196, 199, 242, 247, 292, 301, 318, 324, 332, 347, 349, 350 and/or 353 of the human G6Pase-α (set forth as SEQ ID NO: 2). FIG. 1 shows an alignment of the human and canine G6Pase-α protein sequences, and Table 2 provides a summary of the amino acid differences between human and canine G6Pase-α. The present disclosure contemplates nucleotide substitutions that alter the amino acid sequence at one or more of the residues listed above and in Table 2.

In some examples, the nucleic acid molecule encodes a modified G6Pase-α having an amino acid sequence at least 80%, at least 85%, at least 90%, at least 95%, at least 96%, at least 97%, at least 98% or at least 99% identical to SEQ ID NO: 2, and having a serine to cysteine substitution at amino acid 298. In particular examples, the amino acid sequence of the modified G6Pase-α comprises or consists of SEQ ID NO: 8 (human S298C G6Pase-α). In other particular examples, the amino acid sequence of the modified G6Pase-α comprises or consists of SEQ ID NO: 9 (human S298C/A301V G6Pase-α). In non-limiting examples, the isolated nucleic acid molecule comprises the nucleotide sequence of SEQ ID NO: 6 (modified human G6PC encoding S298C G6Pase-α) or SEQ ID NO: 7 (codon-optimized, modified human G6PC encoding S298C G6Pase-α).

Also provided herein are vectors comprising the isolated nucleic acid molecules encoding modified G6Pase-α. In some embodiments, the nucleic acid molecule encoding the modified G6Pase-α is operably linked to a promoter, such as a G6PC promoter. In some examples, the G6PC promoter is at least 80%, at least 85%, at least 90%, at least 95%, at least 96%, at least 97%, at least 98% or at least 99% identical to nucleotides 182-3045 of SEQ ID NO: 4 (human G6PC promoter/enhancer) or at least 80%, at least 85%, at least 90%, at least 95%, at least 96%, at least 97%, at least 98% or at least 99% identical to 182-3045 of SEQ ID NO: 5 (human codon-optimized G6PC promoter/enhancer). In non-limiting examples, the G6PC promoter comprises nucleotides 182-3045 of SEQ ID NO: 4 or nucleotides 182-3045 of SEQ ID NO: 5.

In some examples, the vector comprises a nucleotide sequence at least 80%, at least 85%, at least 90%, at least 95%, at least 96%, at least 97%, at least 98% or at least 99% identical to nucleotides 182-4441 of SEQ ID NO: 4 or nucleotides 182-4441 of SEQ ID NO: 5. In specific non-limiting examples, the vector comprises nucleotides 182-4441 of SEQ ID NO: 4 or nucleotides 182-4441 of SEQ ID NO: 5.

In some embodiments, the vector is an AAV vector. The AAV serotype can be any suitable serotype for delivery of transgenes to a subject. In some examples, the AAV vector is a serotype 8 AAV (AAV8). In other examples the AAV vector is a serotype 1, 2, 3, 4, 5, 6, 7, 9, 10, 11 or 12 vector (i.e. AAV1, AAV2, AAV3, AAV4, AAV5, AAV6, AAV7, AAV9, AAV10, AAV11 or AAV12). In yet other examples, the AAV vector is a hybrid of two or more AAV serotypes (such as, but not limited to AAV2/1, AAV2/7, AAV2/8 or AAV2/9). The selection of AAV serotype will depend in part on the cell type(s) that are targeted for gene therapy. For treatment of GSD-Ia, the liver and kidney are the relevant target organs.

When an AAV vector is used, the vector can include inverted terminal repeats (ITRs). In some embodiments, the AAV vector comprises a nucleotide sequence at least 80%, at least 85%, at least 90%, at least 95%, at least 96%, at least 97%, at least 98% or at least 99% identical to nucleotides 17-4819 of SEQ ID NO: 4 or nucleotides 17-4819 of SEQ ID NO: 5. In some examples, the AAV vector comprises nucleotides 17-4819 of SEQ ID NO: 4 or nucleotides 17-4819 of SEQ ID NO: 5.

Also provided herein are isolated host cells comprising the nucleic acid molecules or vectors disclosed herein. For example, the isolated host cell can be a cell (or cell line) appropriate for production of recombinant AAV (rAAV). In some examples, the host cell is a mammalian cell, such as a HEK-293, BHK, Vero, RD, HT-1080, A549, Cos-7, ARPE-19, or MRC-5 cell.

Further provided are rAAV comprising a nucleic acid molecule disclosed herein. In some embodiments, the rAAV is rAAV8 and/or rAAV2. However, the AAV serotype can be any other suitable AAV serotype, such as AAV1, AAV2, AAV3, AAV4, AAV5, AAV6, AAV7, AAV9, AAV10, AAV11 or AAV12, or a hybrid of two or more AAV serotypes (such as, but not limited to AAV2/1, AAV2/7, AAV2/8 or AAV2/9). Compositions comprising a rAAV disclosed herein and a pharmaceutically acceptable carrier are also provided by the present disclosure. In some embodiments, the compositions are formulated for intravenous or intramuscular administration. Suitable pharmaceutical formulations for administration of rAAV can be found, for example, in U.S. Patent Application Publication No. 2012/0219528 (herein incorporated by reference).

Further provided are methods of treating a subject diagnosed with a glycogen storage disease, comprising selecting a subject with GSD-Ia and administering to the subject a therapeutically effective amount of a rAAV (or a composition comprising a rAAV) disclosed herein.

Methods of promoting glucose homeostasis; inhibiting hypoglycemia; inhibiting or preventing the development of hepatocellular adenoma (HCA); inhibiting or preventing the development of hepatocellular carcinoma (HCC); inhibiting or preventing renal dysfunction or failure; inhibiting or preventing growth retardation; inhibiting or preventing hepatomegaly; inhibiting or preventing nephromegaly; inhibiting or preventing hyperlipidemia; inhibiting or preventing pulmonary hypertension; or treating, preventing or inhibiting any other complication associated with GSD-Ia, in a subject with a deficiency in glucose-6-phosphatase-α (G6Pase-α) are also provided by the present disclosure. In some embodiments, the methods include administering to the subject a therapeutically effective amount of a rAAV (or a composition comprising a rAAV) disclosed herein. In some embodiments, the subject with a deficiency in G6Pase-α is a subject that has GSD-Ia. Thus, in some examples, the method includes selecting a subject with GSD-Ia.

In some embodiments of the methods disclosed herein, the rAAV is administered intravenously.

In some embodiments, the rAAV is administered at a dose of about $1\times10^{10}$ to about $1\times10^{14}$ viral particles (vp)/kg. In some examples, the rAAV is administered at a dose of about $1\times10^{11}$ to about $8\times10^{13}$ vp/kg or about $1\times10^{12}$ to about $8\times10^{13}$ vp/kg. In other examples, the rAAV is administered at a dose of about $1\times10^{13}$ to about $6\times10^{13}$ vp/kg. In specific non-limiting examples, the rAAV is administered at a dose of at least about $1\times10^{10}$, at least about $5\times10^{10}$, at least about $1\times10^{11}$, at least about $5\times10^{11}$, at least about $1\times10^{12}$, at least about $5\times10^{12}$, at least about $1\times10^{13}$, at least about $5\times10^{13}$, or at least about $1\times10^{14}$ vp/kg. In other non-limiting examples, the rAAV is administered at a dose of no more than about $1\times10^{10}$, no more than about $5\times10^{10}$, no more than about $1\times10^{11}$, no more than about $5\times10^{11}$, no more than about $1\times10^{12}$, no more than about $5\times10^{12}$, no more than about $1\times10^{13}$, no more than about $5\times10^{13}$, or no more than about $1\times10^{14}$ vp/kg. In one non-limiting example, the rAAV is administered at a dose of about $1\times10^{12}$ vp/kg. In another non-limiting example, the rAAV is administered at a dose of about $1\times10^{11}$ vp/kg. The rAAV can be administered in a single dose, or in multiple doses (such as 2, 3, 4, 5, 6, 7, 8, 9 or 10 doses) as needed for the desired therapeutic results.

V. Modified Human G6PC/G6Pase-α Sequences

It is disclosed herein that the canine G6Pase-α enzyme is more active than the human G6Pase-α enzyme. As shown in FIG. 1 and Table 2, the two proteins differ in sequence at 18 residues. Using site-directed mutagenesis, human G6Pase-α mutants with increased phosphohydrolase activity were identified. The human G6Pase-α mutants that were generated contained one or more corresponding amino acids from canine G6Pase-α at position(s) 3, 54, 139, 196, 199, 242, 247, 292, 298, 301, 318, 324, 332, 347, 349, 350 and/or 353 of SEQ ID NO: 2. The human G6Pase-α sequence and a human/canine G6Pase-α consensus sequence are set forth below.

```
Human G6Pase-α (SEQ ID NO: 2):
MEEGMNVLHD FGIQSTHYLQ VNYQDSQDWF ILVSVIADLR NAFYVLFPIW FHLQEAVGIK    60

LLWVAVIGDW LNLVFKWILF GQRPYWWVLD TDYYSNTSVP LIKQFPVTCE TGPGSPSGHA   120

MGTAGVYYVM VTSTLSIFQG KIKPTYRFRC LNVILWLGFW AVQLNVCLSR IYLAAHFPHQ   180

VVAGVLSGIA VAETFSHIHS IYNASLKKYF LITFFLFSFA IGFYLLLKGL GVDLLWTLEK   240

AQRWCEQPEW VHIDTTPFAS LLKNLGTLFG LGLALNSSMY RESCKGKLSK WLPFRLSSIV   300

ASLVLLHVFD SLKPPSQVEL VFYVLSFCKS AVVPLASVSV IPYCLAQVLG QPHKKSL     357

Human/Canine G6Pase-α consensus sequence (SEQ ID NO: 10):
MEXGMNVLHD FGIQSTHYLQ VNYQDSQDWF ILVSVIADLR NAFYVLFPIW FHLXEAVGIK    60

LLWVAVIGDW LNLVFKWILF GQRPYWWVLD TDYYSNTSVP LIKQFPVTCE TGPGSPSGHA   120

MGTAGVYYVM VTSTLSIFXG KXKPTYRFRC LNVILWLGFW AVQLNVCLSR IYLAAHFPHQ   180

VVAGVLSGIA VAETFXHIXS IYNASLKKYF LITFFLFSFA IGFYLLLKGL GVDLLWTLEK   240

AXRWCEXPEW VHIDTTPFAS LLKNLGTLFG LGLALNSSMY RESCKGKLSK WXPFRLSXIV   300

XSLVLLHVFD SLKPPSQXEL VFYXLSFCKS AXVPLASVSV IPYCLAXVXX QPXKKSL     357
```

In some embodiments, provided herein is a modified G6Pase-α comprising SEQ ID NO: 10, wherein X at amino acid residue 3=K or E; X at amino acid residue 54=R or Q; X at amino acid residue 139=R or Q; X at amino acid residue 142=K or I; X at amino acid residue 196=R or S; X at amino acid residue 199=Q or H; X at amino acid residue 242=R or Q; X at amino acid residue 247=R or Q; X at amino acid residue 292=F or L; X at amino acid residue 298=C or S; X at amino acid residue 301=V or A; X at amino acid residue 318=T or V; X at amino acid residue 324=T or V; X at amino acid residue 332=A or V; X at amino acid residue 347=R or Q; X at amino acid residue 349=F or L; X at amino acid residue 350=D or G; or X at amino acid residue 353=D or H, or any combination thereof.

In particular examples, the modified G6Pase-α sequence comprises a S298C mutation, or comprises S298C and A310V mutations, as set forth below. In non-limiting examples, the modified G6Pase-α sequence comprises or consists of SEQ ID NO: 8 or SEQ ID NO: 9.

Human G6Pase-α S298C (SEQ ID NO: 8):
```
MEEGMNVLHD FGIQSTHYLQ VNYQDSQDWF ILVSVIADLR NAFYVLFPIW FHLQEAVGIK    60
LLWVAVIGDW LNLVFKWILF GQRPYWWVLD TDYYSNTSVP LIKQFPVTCE TGPGSPSGHA   120
MGTAGVYYVM VTSTLSIFQG KIKPTYRFRC LNVILWLGFW AVQLNVCLSR IYLAAHFPHQ   180
VVAGVLSGIA VAETFSHIHS IYNASLKKYF LITFFLFSFA IGFYLLLKGL GVDLLWTLEK   240
AQRWCEQPEW VHIDTTPFAS LLKNLGTLFG LGLALNSSMY RESCKGKLSK WLPFRLSCIV   300
ASLVLLHVFD SLKPPSQVEL VFYVLSFCKS AVVPLASVSV IPYCLAQVLG QPHKKSL     357
```

Human G6Pase-α S298C/A310V (SEQ ID NO: 9):
```
MEEGMNVLHD FGIQSTHYLQ VNYQDSQDWF ILVSVIADLR NAFYVLFPIW FHLQEAVGIK    60
LLWVAVIGDW LNLVFKWILF GQRPYWWVLD TDYYSNTSVP LIKQFPVTCE TGPGSPSGHA   120
MGTAGVYYVM VTSTLSIFQG KIKPTYRFRC LNVILWLGFW AVQLNVCLSR IYLAAHFPHQ   180
VVAGVLSGIA VAETFSHIHS IYNASLKKYF LITFFLFSFA IGFYLLLKGL GVDLLWTLEK   240
AQRWCEQPEW VHIDTTPFAS LLKNLGTLFG LGLALNSSMY RESCKGKLSK WLPFRLSCIV   300
VSLVLLHVFD SLKPPSQVEL VFYVLSFCKS AVVPLASVSV IPYCLAQVLG QPHKKSL     357
```

In some embodiments, the modified G6Pase-α comprising an S298C mutation is encoded by a nucleic acid sequence set forth below.

Human G6PC S298C (SEQ ID NO: 6):
```
ATG GAGGAAGGAA TGAATGTTCT CCATGACTTT GGGATCCAGT
CAACACATTA CCTCCAGGTG AATTACCAAG
ACTCCCAGGA CTGGTTCATC TTGGTGTCCG TGATCGCAGA
CCTCAGGAAT GCCTTCTACG TCCTCTTCCC CATCTGGTTC
CATCTTCAGG AAGCTGTGGG CATTAAACTC CTTTGGGTAG
CTGTGATTGG AGACTGGCTC AACCTCGTCT TTAAGTGGAT
TCTCTTTGGA CAGCGTCCAT ACTGGTGGGT TTTGGATACT
GACTACTACA GCAACACTTC CGTGCCCCTG ATAAAGCAGT
TCCCTGTAAC CTGTGAGACT GGACCAGGGA GCCCCTCTGG
CCATGCCATG GGCACAGCAG GTGTATACTA CGTGATGGTC
ACATCTACTC TTTCCATCTT TCAGGGAAAG ATAAAGCCGA
CCTACAGATT TCGGTGCTTG AATGTCATTT TGTGGTTGGG
ATTCTGGGCT GTGCAGCTGA ATGTCTGTCT GTCACGAATC
TACCTTGCTG CTCATTTTCC TCATCAAGTT GTTGCTGGAG
TCCTGTCAGG CATTGCTGTT GCAGAAACTT TCAGCCACAT
CCACAGCATC TATAATGCCA GCCTCAAGAA ATATTTTCTC
ATTACCTTCT TCCTGTTCAG CTTCGCCATC GGATTTTATC
TGCTGCTCAA GGGACTGGGT GTAGACCTCC TGTGGACTCT
GGAGAAAGCC CAGAGGTGGT GCGAGCAGCC AGAATGGGTC
CACATTGACA CCACACCCTT TGCCAGCCTC CTCAAGAACC
TGGGCACGCT CTTTGGCCTG GGGCTGGCTC TCAACTCCAG
CATGTACAGG GAGAGCTGCA AGGGGAAACT CAGCAAGTGG
CTCCCATTCC GCCTCAGCTG CATTGTAGCC TCCCTCGTCC
TCCTGCACGT CTTTGACTCC TTGAAACCCC CATCCCAAGT
CGAGCTGGTC TTCTACGTCT TGTCCTTCTG CAAGAGTGCG
GTAGTGCCCC TGGCATCCGT CAGTGTCATC CCCTACTGCC
TCGCCCAGGT CCTGGGCCAG CCGCACAAGA AGTCGTTGTA A
```

Human codon-optimized G6PC S298C (SEQ ID NO: 7):
```
ATG GAAGAGGGCA TGAACGTGCT GCACGACTTC GGCATCCAGA
GCACCCACTA TCTGCAGGTC AACTACCAGG
ACAGCCAGGA CTGGTTCATC CTGGTGTCCG TGATCGCCGA
CCTGCGGAAC GCCTTCTACG TGCTGTTCCC CATCTGGTTC
CATCTGCAAG AAGCCGTCGG CATCAAGCTG CTGTGGGTGG
CCGTGATCGG CGATTGGCTG AACCTGGTGT TCAAGTGGAT
CCTGTTCGGC CAGCGGCCCT ATTGGTGGGT GCTGGACACC
GACTACTACA GCAACACCAG CGTGCCCCTG ATCAAGCAGT
TCCCCGTGAC CTGCGAGACA GGCCCTGGCT CTCCTTCTGG
CCACGCCATG GGAACAGCCG GCGTGTACTA CGTGATGGTC
ACCAGCACCC TGAGCATCTT CCAGGGCAAG ATCAAGCCCA
CCTACCGGTT CCGGTGCCTG AACGTGATCC TGTGGCTGGG
CTTCTGGGCC GTGCAGCTGA ACGTGTGCCT GAGCCGGATC
TACCTGGCCG CCCACTTCCC ACATCAAGTG GTGGCCGGCG
TGCTGAGCGG AATCGCCGTG GCCGAGACAT TCAGCCACAT
CCACAGCATC TACAACGCCA GCCTGAAGAA GTACTTCCTG
ATCACATTCT TTCTGTTCAG CTTCGCCATC GGCTTCTACC
TGCTGCTGAA GGGCCTGGGC GTGGACCTGC TGTGGACCCT
GGAAAAGGCC CAGCGGTGGT GCGAGCAGCC CGAGTGGGTG
CACATCGACA CCACCCCCTT CGCCAGCCTG CTGAAGAACC
TGGGCACCCT GTTTGGACTG GGCCTGGCCC TGAACAGCAG
CATGTACAGA GAGAGCTGCA AGGGCAAGCT GAGCAAGTGG
```

```
-continued
CTGCCCTTCC GGCTGAGCTG CATCGTGGCC AGCCTGGTGC

TGCTGCACGT GTTCGACAGC CTGAAGCCCC CCAGCCAGGT

GGAACTGGTG TTTTACGTGC TGAGCTTCTG CAAGAGCGCC

GTGGTGCCCC TGGCCTCCGT GTCTGTGATC CCCTACTGCC

TGGCTCAGGT GCTGGGCCAG CCCCACAAGA AGTCCCTCTG A
```

VI. Recombinant AAV for Gene Therapy Applications

AAV belongs to the family Parvoviridae and the genus Dependovirus. AAV is a small, non-enveloped virus that packages a linear, single-stranded DNA genome. Both sense and antisense strands of AAV DNA are packaged into AAV capsids with equal frequency.

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription.

Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, Clin Microbiol Rev 21(4):583-593, 2008).

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, Clin Microbiol Rev 21(4):583-593, 2008).

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, Clin Microbial Rev 21(4):583-593, 2008).

Methods for producing rAAV suitable for gene therapy are well known in the art (see, for example, U.S. Patent Application Nos. 2012/0100606; 2012/0135515; 2011/0229971; and 2013/0072548; and Ghosh et al., Gene Ther 13(4):321-329, 2006), and can be utilized with the recombinant nucleic acid molecules, vectors and methods disclosed herein.

The following examples are provided to illustrate certain particular features and/or embodiments. These examples should not be construed to limit the disclosure to the particular features or embodiments described.

EXAMPLES

Example 1: Construction and Characterization of Human G6PC (G6Pase-α) Mutants for Use in AAV-Mediated Gene Therapy This example describes the generation of 18 human G6PC mutants and the identification of specific G6Pase-α mutants with increased phosphohydrolase activity.

Construction of G6PC Mutants

To construct human G6PC mutants, the pSVL vector, comprising nucleotides 1 to 1074 of human G6PC cDNA (the entire coding region, with the initiation codon ATG at nucleotides 1-3; SEQ ID NO: 11), was used as a template. For PCR-directed mutagenesis, the template was amplified using two outside PCR primers matching nucleotides 1 to 20 (sense) and 1055 to 1074 (antisense) that flanked the 20 nucleotide long sense and antisense mutant primers with the codon to be mutated in the middle (see FIG. 4 and Table 1 below). The template for the hG6PC-S298C/A301V double mutant was the pSVL-hG6PC-S298C mutant. The mutated sequences were cloned in pSVL and verified by DNA sequencing.

TABLE 1

Nucleotide changes in human G6PC mutants

| Mutation | Nucleotide/codon changes | Sequences in human G6PC |
|---|---|---|
| R3K | GAA (R) → AAA (K) | nucleotides 7-9 |
| Q54R | CAG (Q) → CGT (R) | nucleotides 160-162 |
| Q139R | CAG (Q) → CGG (R) | nucleotides 415-417 |
| I142K | ATA (I) → AAA (K) | nucleotides 424-426 |
| S196R | AGC (S) → CGC (R) | Nucleotides 586-588 |
| H199Q | CAC (H) → CAG (Q) | nucleotides 595-597 |
| Q242R | CAG (Q) → AGO (R) | nucleotides 724-726 |
| Q247R | CAG (Q) → CGG (R) | nucleotides 739-741 |
| L292F | CTC (L) → TTC (F) | nucleotides 874-876 |
| S298C | TCT (S)→TGC (C) | nucleotides 892-894 |
| A301V | GCC (A) → GTG (V) | nucleotides 901-903 |
| V318T | GTC (V) → ACT (T) | nucleotides 952-954 |
| V324T | GTC (V) → ACC (T) | nucleotides 970-972 |
| V332A | GTA (V) → GCA (A) | nucleotides 994-996 |
| Q347R | CAG (Q) → CGG (R) | nucleotides 1039-1041 |
| L349F | CTG (L) → TTC (F) | nucleotides 1045-1047 |
| G350D | GGC (G) → GAC (D) | nucleotides 1048-1050 |
| H353D | CAC (H) → GAC (D) | nucleotides 1057-1059 |

Expression in COS-1 Cells and Phosphohydrolase Assays

COS-1 cells were grown at 37° C. in HEPES-buffered Dulbecco modified minimal essential medium supplemented with 4% fetal bovine serum. The G6PC constructs were transfected into COS-1 cells by the DEAE-dextran/chloroquine method. After incubation at 37° C. for 2 days, the transfected cultures were harvested for phosphohydrolase activity. Briefly, reaction mixtures (50 µl) containing 50 mM cacodylate buffer, pH 6.5, 10 mM G6P and appropriate amounts of cell homogenates were incubated at 37° C. for 10 minutes as previously described (Lei et al., Science 262: 580-583, 1993).

Statistical Analysis

The unpaired t test was performed using the GraphPad Prism Program, version 4 (GraphPad Software, San Diego, Calif.). Values were considered statistically significant at $p<0.05$.

Results

The phosphohydrolase activities of human and canine G6Pase-α were compared by in vitro expression assays. The results demonstrated that the canine enzyme was about 5-fold more active than the human enzyme. A sequence alignment of the canine and human sequences showed that the two enzymes differ by 18 amino acid residues (FIG. 1 and Table 2).

TABLE 2

Amino acid differences between human and canine G6Pase-α

|  | Amino acid | Amino acid | Amino acid | Amino acid | Amino acid |
|---|---|---|---|---|---|
| Canine | K3 | R54 | R139 | K142 | R196 |
| Human | E3 | Q54 | Q139 | I142 | S196 |
| Canine | Q199 | R242 | R247 | F292 | C298 |
| Human | H199 | Q242 | Q247 | L292 | S298 |
| Canine | V301 | T318 | T324 | A332 | R347 |
| Human | A301 | V318 | V324 | V332 | Q347 |
| Canine | F349 | D350 | D353 |  |  |
| Human | L349 | G350 | H353 |  |  |

To determine which amino acid substitutions result in increased enzymatic activity of canine G6Pase-α, 18 human G6PC mutants were constructed via site-directed mutagenesis. Each mutant carried one of the corresponding amino acids from canine G6Pase-α. Phosphohydrolase activities of the 18 human G6Pase-α mutants were examined by transient expression assays. The results showed that the human G6PC-S298C construct was the most active, with 2.14-fold higher activity than the activity of the G6PC-WT construct (Table 3). The G6PC-A301V mutant was also more active, being 1.35-fold more active than the G6PC-WT. Next, a double S298C/A301V mutant (hG6PC-S298C/A301V) was constructed. This double mutant was equally as active as the single hG6PC-S298C mutant (Table 3).

TABLE 3

Phosphohydrolase activity of human G6PC mutants

| G6PC construct | Location | Phosphohydrolase activity (nmol/min/mg) |
|---|---|---|
| pSVL-hG6PC-WT |  | 164.5 ± 9.5 (100%) |
| pSVL-hG6PC-E3K | N-terminal | 156.0 ± 6.3 |
| pSVL-hG6PC-Q54R | C1 | 169.6 ± 7.3 |
| pSVL-hG6PC-Q139R | C2 | 113.1 ± 6.7 |
| pSVL-hG6PC-I142K | C2 | 141.0 ± 4.4 |
| pSVL-hG6PC-S196R | H5 | 90.5 ± 2.5 |
| pSVL-hG6PC-H199Q | C3 | 154.0 ± 7.4 |
| pSVL-hG6PC-Q242R | L3 | 174.5 ± 4 |
| pSVL-hG6PC-Q247R | L3 | 143.8 ± 16.4 |
| pSVL-hG6PC-L292F | H8 | 140.3 ± 20.3 |
| pSVL-hG6PC-S298C | H8 | 351.8 ± 16.4 (214%) |
| pSVL-hG6PC-A301V | H8 | 221.7 ± 12.5 (135%) |

TABLE 3-continued

Phosphohydrolase activity of human G6PC mutants

| G6PC construct | Location | Phosphohydrolase activity (nmol/min/mg) |
|---|---|---|
| pSVL-hG6PC-S298C/A301V | H8 | 353.7 ± 18.8 (215%) |
| pSVL-hG6PC-V318T | L4 | 156.7 ± 16.3 |
| pSVL-hG6PC-V324T | H9 | 117.6 ± 8.2 |
| pSVL-hG6PC-V332A | H9 | 160.5 ± 13.1 |
| pSVL-hG6PC-Q347R | C-terminal | 162.5 ± 7.9 |
| pSVL-hG6PC-L349F | C-terminal | 186.4 ± 5.9 (113%) |
| pSVL-hG6PC-G350D | C-terminal | 146.6 ± 16.7 |
| pSVL-hG6PC-H353D | C-terminal | 164.7 ± 2.8 |

Phosphohydrolase activity of COS-1 cells transfected with a human (h) G6PC wild-type (WT) or a hG6PC mutant construct in a pSVL vector. The data represent the mean±SEM. H, L, and C denote the locations of the mutations in helices 1 to 9, luminal loops 1 to 4 or cytoplasmic loops 1 to 4, respectively (FIG. 2). Numbers in parentheses are % of hG6PC-WT activity. Phosphohydrolase assays were performed in duplicate.

It has been previously shown that the structural integrity of transmembrane helices is vital to the stability and enzymatic activity of G6PC, and non-helical mutants play no essential role in the stability of G6PC (Shieh et al., J Biol Chem 277:5047-5053, 2002). In accordance with these previous observations, mutations of amino acid residues in helix 8 of G6PC markedly altered enzymatic activity.

To further confirm the efficacy of the hG6PC-S298C construct, phosphohydrolase activities of two human G6PC constructs, pSVL-G6PC-WT and pSVL-G6PC-S298C, were compared. Transient expression assays showed that the pSVL-G6PC-S298C construct was 1.7-fold more efficacious than the pSVL-G6PC construct (Table 4).

Studies have shown that codon optimization strategies can increase translation efficiency (Huston et al., Mol Ther 9:1867-1877, 2011). Codon-optimized (co) human G6PC is 1.46-fold more active than the G6PC-WT construct (Table 4). To examine the impact of codon optimization, pSVL-co-G6PC-S298C, which expresses a codon optimized human G6PC-S298C, was constructed. Transient expression assays showed that the pSVL-co-G6PC-S298C construct was 2.9-fold more efficacious than the pSVL-G6PC-WT construct (Table 4).

TABLE 4

Phosphohydrolase activity of hG6PC-WT, hG6PC-S298C, co-hG6PC, co-hG6PC-S298C, and canine G6PC

| hG6PC constructs | Phosphohydrolase activity (nmol/min/mg) |
|---|---|
| pSVL-hG6PC-WT | 131.1 ± 3.8 (100%) |
| pSVL-hG6PC-S298C | 223.1 ± 7.1 (170%) |
| pSVL-co- hG6PC | 191.5 ± 6.0 (146%) |
| pSVL-co- hG6PC-S298C | 382.8 ± 23.5 (292%) |
| pSVL-canine G6PC | 725.7 ± 66.5 (554%) |

Phosphohydrolase activity of COS-1 cells transfected with hG6PC-WT, hG6PC-S298C, co-hG6PC, co-hG6PC-S298C, or canine G6PC construct in a pSVL vector. The data represent the mean±SEM of three independent experiments using three separate batches of each construct. Phosphohydrolase assays were performed in duplicate. Numbers in parentheses are % of hG6PC-WT activity.

Figure 3:
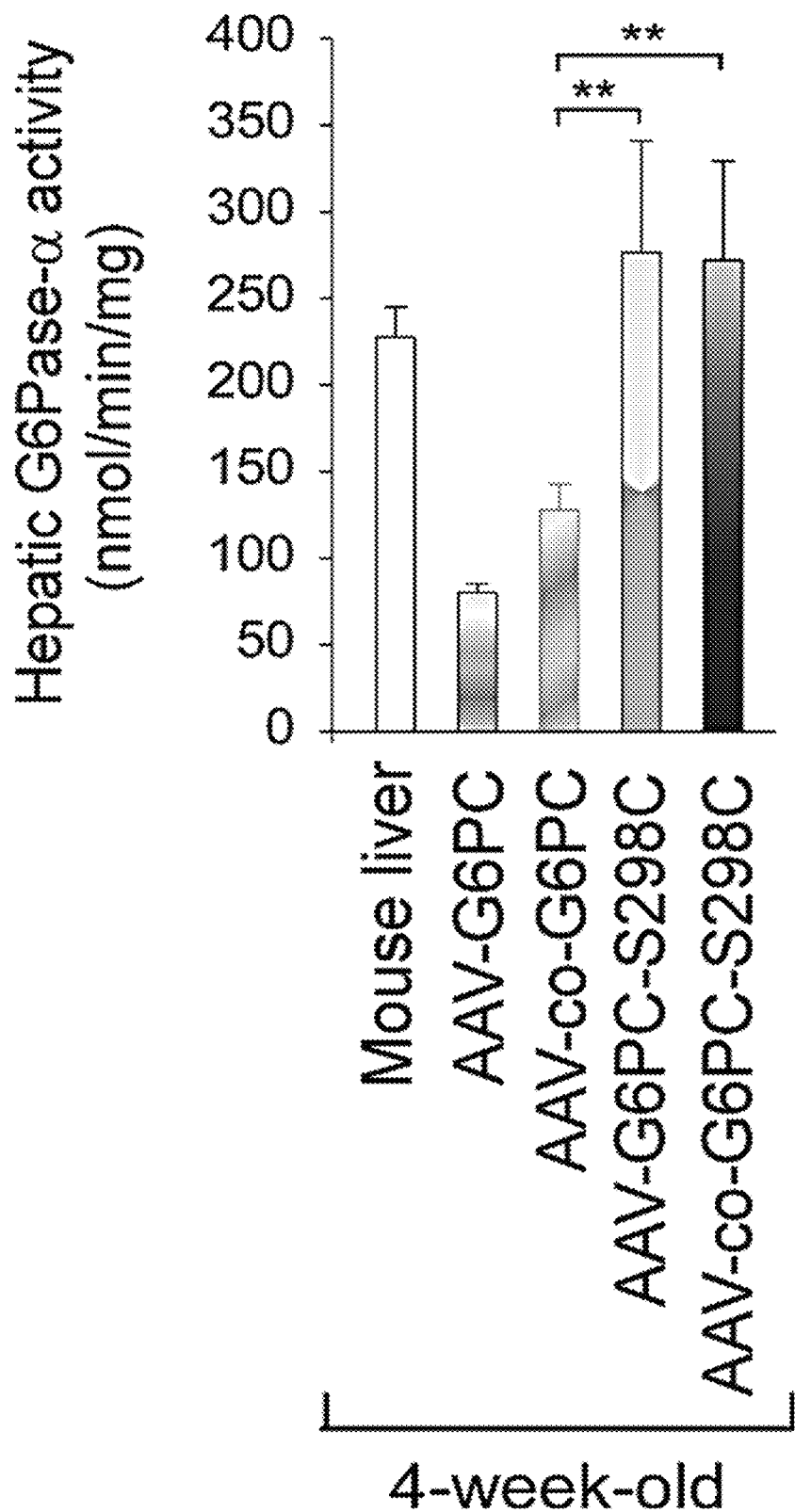
FIG. 3 is a graph showing hepatic microsomal G6Pase-α activity in 4-week-old GSD-Ia (G6pc$^{-/-}$) mice transduced at age 2 weeks with a recombinant AAV8-GPE vector ($10^{13}$ vg/kg) expressing human G6PC (AAV-G6PC), codon-optimized (co) human G6PC (AAV-co-G6PC), human G6PC-S298C mutant (AAV-G6PC-S298C), or co-human G6PC-S298C mutant (AAV-co-G6PC-S298C). Hepatic microsomal G6Pase-α activity in 4-week-old wild type mice averaged 227.5±17.6 nmol/min/mg. Data are presented as the mean±SEM. **P<0.005.

Recombinant AAV8-GPE-G6PC, AAV8-GPE-co-G6PC, AAV8-GPE-G6PC-S298C and AAV8-GPE-co-G6PC-S298C vectors were constructed. Hepatic G6Pase activity was examined in GSD-Ia (G6pc–/–) mice infused with AAV8-GPE-G6PC, AAV8-GPE-G6PC-S298C, AAV8-GPE-co-G6PC, or AAV8-GPE-co-G6PC-S298C vectors. In agreement with in vitro expression studies, in vivo studies showed that the AAV8-GPE-G6PC-S298C and AAV8-co-G6PC-S298C vectors directed hepatic G6PC expression that was 3.4-fold over that of the AAV8-GPE-G6PC vector (FIG. 3).

Example 2: Evaluation of Minimal Vector Dose Required to Correct Hepatic G6Pase-α Deficiency This example describes studies to determine the minimal dose needed to restore G6Pase-α activity to a level that prevents HCA/HCC development and maintains glucose homeostasis. GSD-Ia is characterized by impaired glucose homeostasis and the long-term complication of hepatocellular adenoma (HCA) (Chou et al., *Nat Rev Endocrinol* 6:676-688, 2010). The inventor has previously shown that rAAV8-G6PC-treated G6pc–/– mice expressing >3% of normal hepatic G6Pase-α activity (which is equivalent to >5 units of G6Pase-α activity; 1 nmol/min/mg is defined as one unit of G6Pase-α activity) maintain glucose homeostasis to age P70-P90 weeks and do not develop HCA (Lee et al., *Hepatology* 56:1719-1729, 2012; PCT Publication No. WO 2015/081101, which is herein incorporated by reference).

Figure 5:
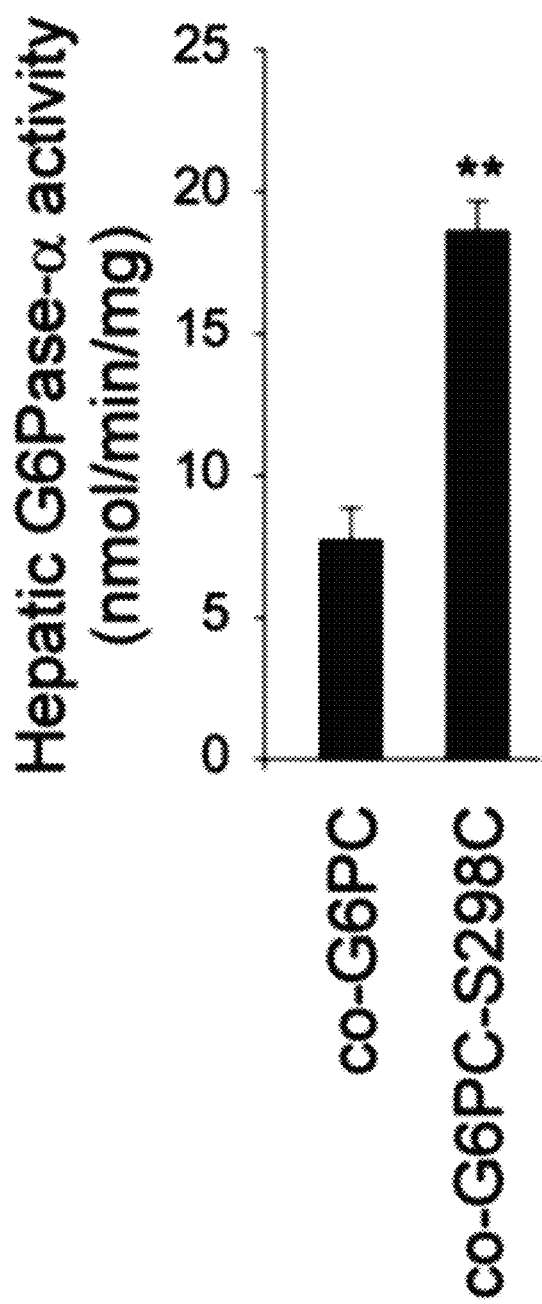
FIG. 5 is a graph showing hepatic G6Pase-α activity in 24-day-old G6pc$^{-/-}$ mice transduced at age 10 days with $5\times10^{11}$ vg/kg AAV-co-G6PC vector (n=3) or rAAV8-co-G6PC-S298C vector (n=3). Wild-type hepatic G6Pase activity averaged 174±18.3 nmol/min/mg. Data represent the mean±SEM. **P<0.005.

The present study was conducted using purified, accurately tittered rAAV8 vectors (supplied by Dimension Therapeutics, Cambridge, Mass.) to determine the minimal dosage of rAAV vector required to correct hepatic G6Pase-α deficiency using G6pc–/– mice. Ten-day-old G6pc–/– mice were infused with $5 \times 10^{11}$ vg/kg of rAAV8-co-G6PC or rAAV8-co-G6PC-S298C. At age 24-days (2 weeks post-infusion), hepatic G6Pase-α activity in rAAV-co-G6PC-S298C- and rAAV8-co-G6PC-treated G6pc–/– mice was 18.6±1.1 and 7.7±1.1 units, respectively (FIG. 5).

It has been shown that the efficiency and persistence of AAV-mediated hepatic gene transfer are lower during early development because the fast rate of hepatocellular proliferation associated with liver growth can dilute out the number of cells effectively infected with AAV (Yiu et al., *Mol Ther* 18:1076-1084, 2010). In two-week-old G6pc–/– mice infused with $1.5 \times 10^{13}$ vg/kg of rAAV-G6PC, hepatic G6Pase-α activity was 174.0±22.4 units at age 24 weeks. In four-week-old G6pc–/– mice infused with $1 \times 10^{13}$ vg/kg of rAAV-G6PC, hepatic G6Pase-α activity was 335.6±40.2 units at age 24 weeks, which is 2.9-fold higher than the G6Pase-α activity in mice infused at age 2 weeks with the same vector dosage.

Therefore, it is expected that if the same dosage of rAAV-co-G6PC-S298C is infused into 4-week-old G6pc–/– mice, hepatic G6Pase-α activity will be restored to 53.94 (18.6×2.9) units at age 24 weeks, well above the minimal hepatic G6Pase-α activity (5 units) required to maintain glucose homeostasis and prevent HCA/HCC formation. This also meets the requirement of rAAV-mediated human clinical gene therapy trial for the treatment of GSD-Ia, which requires administration of <$1 \times 10^{12}$ vg/kg AAV.

To compare the relative efficacy of the four different vectors, 10-day-old G6pc–/– mice are infused with $5 \times 10^{11}$ vg/kg of accurately tittered rAAV8-G6PC or rAAV8-G6PC-S298C vector and hepatic G6Pase-α activity of the treated G6pc–/– mice is examined at age 24 days. In addition, 10-day-old G6pc–/– mice are infused with $5 \times 10^{12}$ vg/kg of accurately tittered rAAV8-G6PC, rAAV8-G6PC-S298C, rAAV8-co-G6PC or rAAV8-co-G6PC-S298C and hepatic G6Pase-α activity of the treated G6pc–/– mice is examined at age 12 weeks. The results of this study will demonstrate the stability of transgene expression from age 24 days to age 12 weeks.

Untreated G6pc–/– mice have a short lifespan. To more accurately determine the minimal dosage of rAAV vector required to correct hepatic G6Pase-α deficiency in adult mice, L-G6pc–/– mice, which have a liver-specific G6Pase knockout and survive to adulthood, were used as described below.

G6pc$^{fx/fx}$ mice contain exon 3 of the G6pc gene flanked with loxP sites (Peng et al., *Genesis* 47:590-594, 2009). The G6pc$^{fx/fx}$ mice were crossed with SA$^{creERT2/w}$ mice (Schuler et al., *Genesis* 39:167-172, 2004), which express a tamoxifen-dependent Cre-recombinase under the control of the serum albumin promoter to produce G6pc$^{fx/fx}$.SA$^{creERT2/w}$ mice. The liver-specific G6pc knockout (L-G6pc–/–) were generated by tamoxifen-mediated excision of the G6pc exon 3 in three-week-old G6pc$^{fx/fx}$.SA$^{creERT2/w}$ mice. It is expected that 100% of L-G6pc–/– mice will develop HCA/HCC at age 54 weeks (51 week post G6pc gene excision).

Figure 6A:
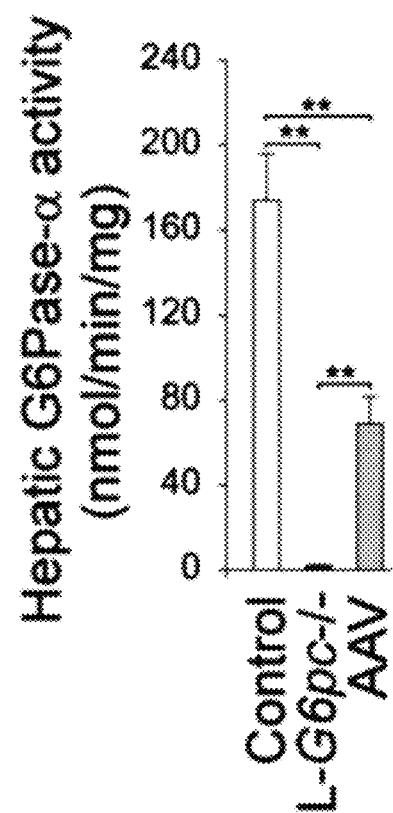
FIGS. 6A-6E show data demonstrating correction of hepatic G6Pase-α deficiency by rAAV-G6PC. L-G6pc$^{-/-}$ mice were treated $1\times10^{12}$ vg/kg of rAAV-G6PC at age 10 weeks and analyzed at age 18 weeks.
Figure 6B:
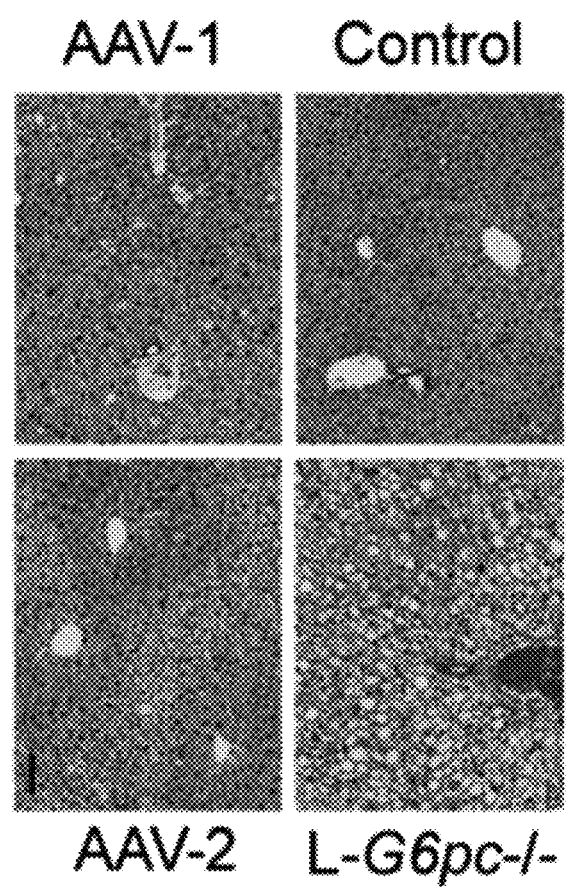
Figure 6C:
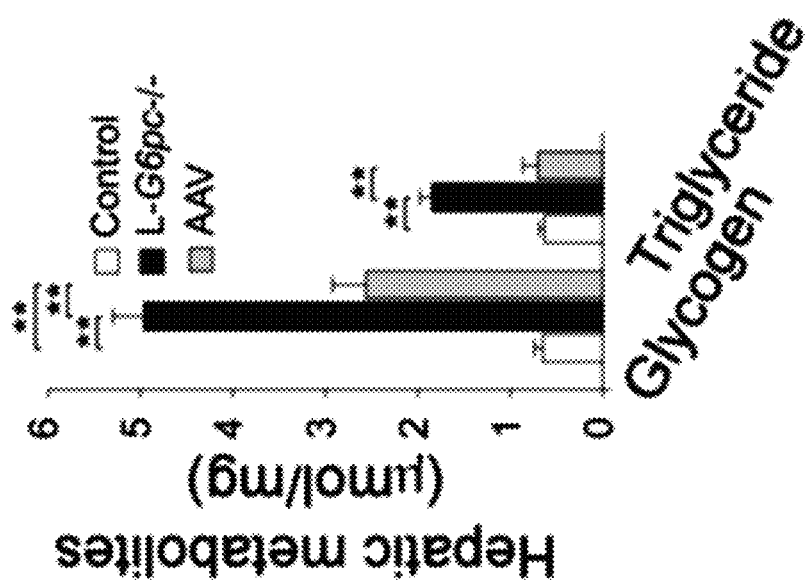
Figure 6D:
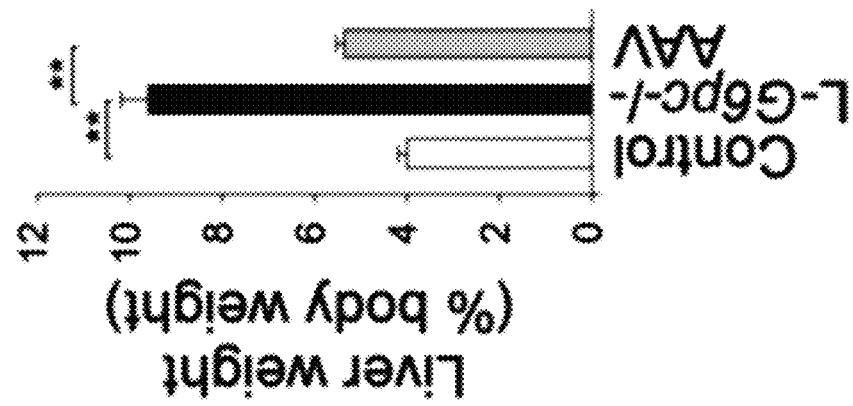
Figure 6E:
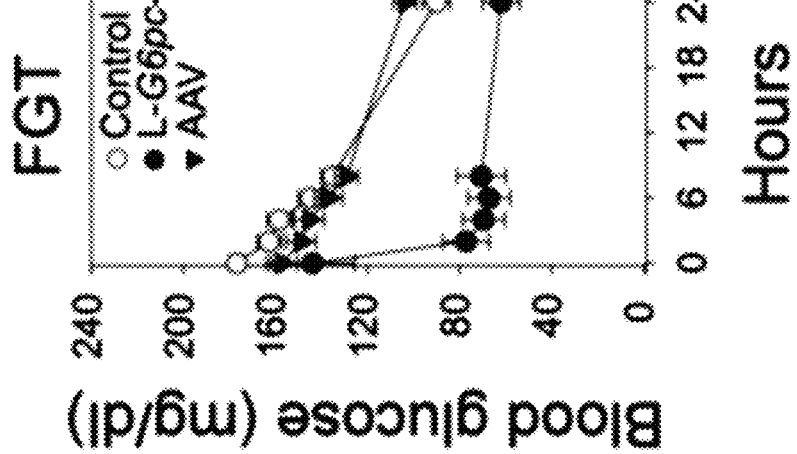

Ten-week-old L-G6pc–/– mice were treated with $10^{12}$ vg/kg of rAAV-G6PC. The results showed that at age 18 weeks, hepatic G6Pase-α activity was restored to 68.9±12.8 units (FIG. 6A). The AAV-treated mice (AAV mice) exhibited no hepatic histological abnormalities except mild glycogen storage (FIG. 6B), and displayed a normal profile of fasting glucose tolerance (FGT) (FIG. 6C). Moreover, the AAV mice exhibited normalized liver weight (FIG. 6D) and normalized hepatic levels of glycogen and triglyceride (FIG. 6E). These data indicate that it is possible to scale down to a more optimal dosage for a human clinical gene therapy trial for the treatment of GSD-Ia.

To examine the minimal dosage of rAAV8-G6PC, rAAV8-co-G6PC, rAAV8-G6PC-S298C and rAAV8-co-G6PC-S298C required to correct hepatic G6Pase-α deficiency and prevent HCA/HCC development, various doses (e.g., $1 \times 10^{10}$, $3 \times 10^{10}$, $1 \times 10^{11}$, $3 \times 10^{11}$, $1 \times 10^{12}$, $3 \times 10^{12}$ and $1 \times 10^{13}$) of each vector are infused into 10-12-week-old L-G6pc–/– mice. At age 54 weeks, G6Pase-α activity is measured. Hepatic histology, FGT, liver weight and hepatic levels of glycogen and triglyceride are also measured and/or evaluated.

Example 3: Treatment of Human GSD-Ia Using AAV-Based Gene Therapy

This example describes an exemplary method for the clinical use of AAV vectors encoding modified G6PC for the treatment of GSD-Ia.

A patient diagnosed with GSD-Ia is selected for treatment. Typically the patient is at least 18 years old and may or may not have had pre-exposure to immunomodulation. The patient is administered a therapeutically effective amount of a recombinant AAV expressing modified G6PC, such as a rAAV comprising SEQ ID NO: 4 or SEQ ID NO: 5, as disclosed herein. The recombinant AAV can be administered intravenously. An appropriate therapeutic dose can be selected by a medical practitioner. In some cases, the therapeutically effective dose is in the range of $1 \times 10^{10}$ to $1 \times 10^{14}$ viral particles (vp)/kg, such as about $1 \times 10^{11}$ or $1 \times 10^{12}$ vp/kg. In most instances, the patient is administered a single dose. In the absence of immunomodulation, the patient is likely to tolerate only a single infusion of rAAV. If the subject has had pre-exposure immunomodulation, two or more doses may be administered. The health of the subject can be monitored over time to determine the effectiveness of the treatment.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A recombinant AAV (rAAV) comprising a nucleic acid molecule encoding a modified glucose-6-phosphatase-α (G6Pase-α), wherein the modified G6Pase-α comprises a serine to cysteine substitution at amino acid 298 of human G6Pase-α (SEQ ID NO: 2), and wherein the nucleic acid molecule encoding the modified G6Pase-α is operably linked to a promoter.

2. The rAAV of claim 1, wherein the amino acid sequence of the modified G6Pase-α comprises or consists of SEQ ID NO: 8.

3. The rAAV of claim 1, wherein the nucleic acid molecule comprises the nucleotide sequence of SEQ ID NO: 6 or SEQ ID NO: 7.

4. The rAAV of claim 1, wherein the promoter comprises a G6PC promoter.

5. The rAAV of claim 4, wherein the G6PC promoter comprises nucleotides 182-3045 of SEQ ID NO: 4 or nucleotides 182-3045 of SEQ ID NO: 5.

6. The rAAV of claim 1, wherein the nucleic acid molecule comprises nucleotides 182-4441 of SEQ ID NO: 4 or nucleotides 182-4441 of SEQ ID NO: 5.

7. The rAAV of claim 1, wherein the nucleic acid molecule comprises nucleotides 17-4819 of SEQ ID NO: 4 or nucleotides 17-4819 of SEQ ID NO: 5.

8. The rAAV of claim 1, wherein the rAAV is rAAV8.

9. A composition comprising the rAAV of claim 1 in a pharmaceutically acceptable carrier.

10. The composition of claim 9 formulated for intravenous administration.

* * * * *

SEQUENCE LISTING

```
<160> NUMBER OF SEQ ID NOS: 11

<210> SEQ ID NO 1
<211> LENGTH: 357
<212> TYPE: PRT
<213> ORGANISM: Canis lupus

<400> SEQUENCE: 1

Met Glu Lys Gly Met Asp Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Arg Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Met Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
            115                 120                 125

Val Met Val Thr Ser Thr Leu Ser Ile Phe Arg Gly Arg Lys Arg Pro
    130                 135                 140

Thr Tyr Arg Phe Arg Cys Leu Asn Ile Leu Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Arg His Ile Gln Ser Ile Tyr Asn Ala Ser Leu Lys Lys
            195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Arg Arg Trp Cys Glu Arg Pro Glu Trp Val His Ile Asp Thr Thr
                245                 250                 255

Pro Phe Ala Ser Leu Leu Lys Asn Val Gly Thr Leu Phe Gly Leu Gly
            260                 265                 270

Val Thr Leu Asn Ser Ser Met Tyr Arg Glu Ser Cys Lys Gly Lys Leu
            275                 280                 285

Ser Lys Trp Phe Pro Phe Arg Leu Ser Cys Ile Val Val Ser Leu Ile
    290                 295                 300

Leu Leu His Leu Phe Asp Ser Leu Lys Pro Pro Ser Gln Thr Glu Leu
305                 310                 315                 320

Ile Phe Tyr Thr Leu Ser Phe Cys Lys Ser Ala Ala Val Pro Leu Ala
```

```
                        325             330             335
Ser Val Ser Leu Ile Pro Tyr Cys Leu Ala Arg Val Phe Asp Gln Pro
                340             345             350
Asp Lys Lys Ser Leu
        355

<210> SEQ ID NO 2
<211> LENGTH: 357
<212> TYPE: PRT
<213> ORGANISM: Homo sapiens

<400> SEQUENCE: 2

Met Glu Glu Gly Met Asn Val Leu His Asp Phe Gly Ile Gln Ser Thr
1               5                   10                  15
His Tyr Leu Gln Val Asn Tyr Gln Asp Ser Gln Asp Trp Phe Ile Leu
            20                  25                  30
Val Ser Val Ile Ala Asp Leu Arg Asn Ala Phe Tyr Val Leu Phe Pro
        35                  40                  45
Ile Trp Phe His Leu Gln Glu Ala Val Gly Ile Lys Leu Leu Trp Val
    50                  55                  60
Ala Val Ile Gly Asp Trp Leu Asn Leu Val Phe Lys Trp Ile Leu Phe
65                  70                  75                  80
Gly Gln Arg Pro Tyr Trp Trp Val Leu Asp Thr Asp Tyr Tyr Ser Asn
                85                  90                  95
Thr Ser Val Pro Leu Ile Lys Gln Phe Pro Val Thr Cys Glu Thr Gly
            100                 105                 110
Pro Gly Ser Pro Ser Gly His Ala Met Gly Thr Ala Gly Val Tyr Tyr
        115                 120                 125
Val Met Val Thr Ser Thr Leu Ser Ile Phe Gln Gly Lys Ile Lys Pro
    130                 135                 140
Thr Tyr Arg Phe Arg Cys Leu Asn Val Ile Leu Trp Leu Gly Phe Trp
145                 150                 155                 160
Ala Val Gln Leu Asn Val Cys Leu Ser Arg Ile Tyr Leu Ala Ala His
                165                 170                 175
Phe Pro His Gln Val Val Ala Gly Val Leu Ser Gly Ile Ala Val Ala
            180                 185                 190
Glu Thr Phe Ser His Ile His Ser Ile Tyr Asn Ala Ser Leu Lys Lys
        195                 200                 205
Tyr Phe Leu Ile Thr Phe Phe Leu Phe Ser Phe Ala Ile Gly Phe Tyr
    210                 215                 220
Leu Leu Leu Lys Gly Leu Gly Val Asp Leu Leu Trp Thr Leu Glu Lys
225                 230                 235                 240
Ala Gln Arg Trp Cys Glu Gln Pro Glu Trp Val His Ile Asp Thr Thr
                245                 250                 255
Pro Phe Ala Ser Leu Leu Lys Asn Leu Gly Thr Leu Phe Gly Leu Gly
            260                 265                 270
Leu Ala Leu Asn Ser Ser Met Tyr Arg Glu Ser Cys Lys Gly Lys Leu
        275                 280                 285
Ser Lys Trp Leu Pro Phe Arg Leu Ser Ser Ile Val Ala Ser Leu Val
    290                 295                 300
Leu Leu His Val Phe Asp Ser Leu Lys Pro Pro Ser Gln Val Glu Leu
305                 310                 315                 320
Val Phe Tyr Val Leu Ser Phe Cys Lys Ser Ala Val Pro Leu Ala
                325                 330                 335
```

```
Ser Val Ser Val Ile Pro Tyr Cys Leu Ala Gln Val Leu Gly Gln Pro
        340                 345                 350

His Lys Lys Ser Leu
        355

<210> SEQ ID NO 3
<211> LENGTH: 7671
<212> TYPE: DNA
<213> ORGANISM: Artificial Sequence
<220> FEATURE:
<223> OTHER INFORMATION: Synthetic construct (pTR-GPE-human G6PC)
<220> FEATURE:
<221> NAME/KEY: misc_feature
<222> LOCATION: (17)..(163)
<223> OTHER INFORMATION: Inverted terminal repeat
<220> FEATURE:
<221> NAME/KEY: misc_feature
<222> LOCATION: (182)..(3045)
<223> OTHER INFORMATION: GPE
<220> FEATURE:
<221> NAME/KEY: misc_feature
<222> LOCATION: (3051)..(3184)
<223> OTHER INFORMATION: Stuffer sequence
<220> FEATURE:
<221> NAME/KEY: misc_feature
<222> LOCATION: (3185)..(3321)
<223> OTHER INFORMATION: Intron
<220> FEATURE:
<221> NAME/KEY: misc_feature
<222> LOCATION: (3322)..(3367)
<223> OTHER INFORMATION: Stuffer sequence
<220> FEATURE:
<221> NAME/KEY: misc_feature
<222> LOCATION: (3368)..(4441)
<223> OTHER INFORMATION: human G6PC coding sequence
<220> FEATURE:
<221> NAME/KEY: misc_feature
<222> LOCATION: (4674)..(4819)
<223> OTHER INFORMATION: Inverted terminal repeat

<400> SEQUENCE: 3
gggggggggg gggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctagatctg aattcggtac     180 cccttttgaga atccacggtg tctcgatgca gtcagctttc taacaagctg gggcctcacc    240
tgttttccca cggataaaaa cgtgctggag gaagcagaaa ggggctggca ggtgaaaga     300 tgaggaccag ctcatcgtct catgactatg aggttgctct gatccagagg gtcccctgc     360 ctggtggccc accgccagga agactcccac tgtccctgga tgcccagagt gggatgtcaa    420
ctccatcact tatcaactcc ttatccatag gggtattctt cctgaggcgt ctcagaaaac    480
agggccctcc ccatatgctg accacataat agaacccctc ccaactcaga cccctggct     540 gctagctgcc ctggcatgac ccagacagtg gcctttgtat atgttttag actcaccttg     600 actcacctct gaccatagaa actctcatcc cagaggtcac tgcaatagtt actccacaac    660
agaggcttat ctgggtagag ggaggctccc tacctatggc ccagcagccc tgacagtgca    720
gatcacatat accccacgcc ccagcactgc ctgccacgca tgggcttact ttacacccac    780
ccacagtcac caaacacatta cctgctctcc aaggttaggc gtggcaggag aagtttgctt    840
ggaccagcag aaaccatgca gtcaaggaca actggagtca gcatgggctg ggtgcgagcc    900
cttggtgggg tggggaggag actccaggtc atacctcctg gaggatgttt taatcatttc    960
cagcatggaa tgctgtcaac ttttgccaca gattcattag ctctgagttt cttttttctg   1020
tccccagcta cccccttacat gtcaatatgg acttaatgat gggaaattca ggcaagtttt   1080
```

```
taaacatttt attccccctg gctcttatcc tcaaaaaatg catgaatttg gaggcagtgg    1140
ctcatgcctg taatcccaat gctttgctag gttgaggcgg gaggatcact tgaagccagg    1200
aatttgagac cagcctgggc cgcatagtga gaccccgttt ctacaaaaat aaataaataa    1260
ataataaata atagtgatat gaagcatgat taaatagccc tatttttaaa aatgcatgag    1320
ttcgttacct gattcattcc ctggttcctt tcacagtcct ccgtgaccca agtgttaggg    1380
ttttggtctc tctactattt gtaggctgat atatagtata cacacacaca cacacacaca    1440
tatacacaca cacagtgtat cttgagcttt cttttgtata tctacacaca tatgtataag    1500
aaagctcaag atatagaagc cctttttcaa aaataactga aagtttcaaa ctctttaagt    1560
ctccagttac cattttgctg gtattcttat ttggaaccat acattcatca tattgttgca    1620
cagtaagact atacattcat tattttgctt aaacgtatga gttaaaacac ttggccaggc    1680
atggtggttc acacctgtaa tcccagagct ttgggaagcc aagactggca gatctcttga    1740
gctcaggaat tcaagaccag cctgggcaac atggaaaaac cccatctcta caaaagatag    1800
aaaaattagc caggcatggt ggcgtgtgcc tgtggtccca gctactcagg aggctgaggt    1860
gggaggatca cattagccca ggaggttgag gctgcagtga gccgtgatta tgccactgca    1920
ctccagcctg ggagacagag tgagaccctg tttcaaaaaa aagagagaga aaatttaaaa    1980
aagaaaacaa caccaagggc tgtaacttta aggtcattaa atgaattaat cactgcattc    2040
aaaaacgatt actttctggc cctaagagac atgaggccaa taccaggaag ggggttgatc    2100
tcccaaacca gaggcagacc ctagactcta atacagttaa ggaaagacca gcaagatgat    2160
agtccccaat acaatagaag ttactatatt ttatttgttg ttttttcttt gttttgtttt    2220
gttttgtttt gttttgtttt agagactggg gtcttgctcg attgcccagg ctgtagtgca    2280
gcggtgggac aatagctcac tgcagactcc aactcctggg ctcaagcaat cctcctgcct    2340
cagcctcctg aatagctggg actacaaggg tacaccatca cacacaccaa aacaatttt    2400 taaattttg tgtagaaacg agggtcttgc tttgttgccc aggctggtct ccaactcctg    2460
gcttcaaggg atcctcccac ctcagcctcc caaattgctg ggattacagg tgtgagccac    2520
cacaaccagc cagaacttta ctaatttta aattaagaac ttaaaacttg aatagctaga    2580
gcaccaagat ttttctttgt ccccaaataa gtgcagttgc aggcatagaa aatctgacat    2640
ctttgcaaga atcatcgtgg atgtagactc tgtcctgtgt ctctggcctg gtttcgggga    2700
ccaggagggc agaccttgc actgccaaga agcatgccaa agttaatcat tggccctgct    2760
gagtacatgc ccgatcaggc tgtttttgtg tgcctgtttt tctatttac gtaaatcacc    2820 ctgaacatgt ttgcatcaac ctactggtga tgcacctttg atcaatacat tttagacaaa    2880
cgtggttttt gagtccaaag atcagggctg ggttgacctg aatactggat acagggcata    2940
taaaacaggg gcaaggcaca gactcatagc agagcaatca ccaccaagcc tggaataact    3000
gcaagggctc tgctgacatc ttcctgaggt gccaaggaaa tgaggtctag agaagcttta    3060
ttgcggtagt ttatcacagt taaattgcta acgcagtcag tgcttctgac acaacagtct    3120
cgaacttaag ctgcagtgac tctcttaagg tagccttgca gaagttggtc gtgaggcact    3180
gggcaggtaa gtatcaaggt tacaagacag gtttaaggag accaatagaa actgggcttg    3240
tcgagacaga gaagactctt gcgtttctga taggcaccta ttggtcttac tgacatccac    3300
tttgcctttc tctccacagg tgtccactcc cagttcaatt acagctctta aggccctgca    3360
ggccaccatg gaggaaggaa tgaatgttct ccatgacttt gggatccagt caacacatta    3420
```

```
cctccaggtg aattaccaag actcccagga ctggttcatc ttggtgtccg tgatcgcaga   3480
cctcaggaat gccttctacg tcctcttccc catctggttc catcttcagg aagctgtggg   3540
cattaaactc ctttgggtag ctgtgattgg agactggctc aacctcgtct ttaagtggat   3600
tctctttgga cagcgtccat actggtgggt tttggatact gactactaca gcaacacttc   3660
cgtgcccctg ataaagcagt tccctgtaac ctgtgagact ggaccaggga gccctctgg    3720 ccatgccatg ggcacagcag gtgtatacta cgtgatggtc acatctactc tttccatctt   3780
tcagggaaag ataaagccga cctacagatt tcggtgcttg aatgtcattt tgtggttggg   3840
attctgggct gtgcagctga atgtctgtct gtcacgaatc taccttgctg ctcattttcc   3900
tcatcaagtt gttgctggag tcctgtcagg cattgctgtt gcagaaactt tcagccacat   3960
ccacagcatc tataatgcca gcctcaagaa atatttctc attaccttct tcctgttcag    4020
cttcgccatc ggattttatc tgctgctcaa gggactgggt gtagacctcc tgtggactct   4080
ggagaaagcc cagaggtggt gcgagcagcc agaatgggtc cacattgaca ccacacccctt  4140 tgccagcctc ctcaagaacc tgggcacgct ctttggcctg ggctggctc tcaactccag    4200 catgtacagg gagagctgca agggaaaact cagcaagtgg ctcccattcc gcctcagctc   4260
tattgtagcc tccctcgtcc tcctgcacgt cttttgactcc ttgaaacccc catcccaagt  4320
cgagctggtc ttctacgtct tgtccttctg caagagtgcg gtagtgcccc tggcatccgt   4380
cagtgtcatc ccctactgcc tcgcccaggt cctgggccag ccgcacaaga agtcgttgta   4440
agcggccgcg gggatccaga catgataaga tacattgatg agtttggaca aaccacaact   4500
agaatgcagt gaaaaaaatg ctttatttgt gaaatttgtg atgctattgc tttatttgta   4560
accattataa gctgcaataa acaagttaac aacaacaatt gcattcattt tatgtttcag   4620 gttcagggg aggtgtggga ggttttttag tcgaccatgc tggggagaga tctaggaacc    4680
cctagtgatg gagttggcca ctccctctct gcgcgctcgc tcgctcactg aggccgcccg   4740
ggcaaagccc gggcgtcggg cgacctttgg tcgcccggcc tcagtgagcg agcgagcgcg   4800
cagagaggga gtggccaacc ccccccccccc cccccctgca gccctgcatt aatgaatcgg   4860
ccaacgcgcg gggagaggcg gtttgcgtat tgggcgctct tccgcttcct cgctcactga   4920
ctcgctgcgc tcggtcgttc ggctgcggcg agcggtatca gctcactcaa aggcggtaat   4980
acggttatcc acagaatcag gggataacgc aggaaagaac atgtgagcaa aaggccagca   5040
aaaggccagg aaccgtaaaa aggccgcgtt gctggcgttt ttccataggc tccgcccccc   5100
tgacgagcat cacaaaaatc gacgctcaag tcagaggtgg cgaaacccga caggactata   5160
aagataccag gcgtttcccc ctggaagctc cctcgtgcgc tctcctgttc cgaccctgcc   5220
gcttaccgga tacctgtccg cctttctccc ttcgggaagc gtggcgcttt ctcaatgctc   5280
acgctgtagg tatctcagtt cggtgtaggt cgttcgctcc aagctgggct gtgtgcacga   5340
accccccgtt cagcccgacc gctgcgcctt atccggtaac tatcgtcttg agtccaaccc   5400
ggtaagacac gacttatcgc cactggcagc agccactggt aacaggatta gcagagcgag   5460
gtatgtaggc ggtgctacag agttcttgaa gtggtggcct aactacggct acactagaag   5520
gacagtattt ggtatctgcg ctctgctgaa gccagttacc ttcggaaaaa gagttggtag   5580
ctcttgatcc ggcaaacaaa ccaccgctgg tagcggtggt ttttttgttt gcaagcagca   5640
gattacgcgc agaaaaaaag gatctcaaga agatcctttg atcttttcta cggggtctga   5700
cgctcagtgg aacgaaaact cacgttaagg gattttggtc atgagattat caaaaaggat   5760
cttcacctag atccttttaa attaaaaatg aagttttaaa tcaatctaaa gtatatatga   5820
```

-continued

```
gtaaacttgg tctgacagtt accaatgctt aatcagtgag gcacctatct cagcgatctg    5880
tctatttcgt tcatccatag ttgcctgact ccccgtcgtg tagataacta cgatacggga    5940
gggcttacca tctggcccca gtgctgcaat gataccgcga gacccacgct caccggctcc    6000
agatttatca gcaataaacc agccagccgg aagggccgag cgcagaagtg gtcctgcaac    6060
tttatccgcc tccatccagt ctattaattg ttgccgggaa gctagagtaa gtagttcgcc    6120
agttaatagt ttgcgcaacg ttgttgccat tgctacaggc atcgtggtgt cacgctcgtc    6180
gtttggtatg gcttcattca gctccggttc ccaacgatca aggcgagtta catgatcccc    6240
catgttgtgc aaaaaagcgg ttagctcctt cggtcctccg atcgttgtca gaagtaagtt    6300
ggccgcagtg ttatcactca tggttatggc agcactgcat aattctctta ctgtcatgcc    6360
atccgtaaga tgcttttctg tgactggtga gtactcaacc aagtcattct gagaatagtg    6420
tatgcggcga ccgagttgct cttgcccggc gtcaatacgg gataataccg cgccacatag    6480
cagaacttta aaagtgctca tcattggaaa acgttcttcg gggcgaaaac tctcaaggat    6540
cttaccgctg ttgagatcca gttcgatgta acccactcgt gcacccaact gatcttcagc    6600
atcttttact ttcaccagcg tttctgggtg agcaaaaaca ggaaggcaaa atgccgcaaa    6660
aaagggaata agggcgacac ggaaatgttg aatactcata ctcttccttt ttcaatatta    6720
ttgaagcatt tatcagggtt attgtctcat gagcggatac atatttgaat gtatttagaa    6780
aaataaacaa ataggggttc cgcgcacatt tccccgaaaa gtgccacctg acgtctaaga    6840
aaccattatt atcatgacat taacctataa aaataggcgt atcacgaggc cctttcgtct    6900
cgcgcgtttc ggtgatgacg gtgaaaacct ctgacacatg cagctcccgg agacggtcac    6960
agcttgtctg taagcggatg ccgggagcag acaagcccgt cagggcgcgt cagcgggtgt    7020
tggcgggtgt cggggctggc ttaactatgc ggcatcagag cagattgtac tgagagtgca    7080
ccatatgcgg tgtgaaatac cgcacagatg cgtaaggaga aaataccgca tcaggaaatt    7140
gtaaacgtta atattttgtt aaaattcgcg ttaaattttt gttaaatcag ctcattttt    7200 aaccataggg ccgaaatcgg caaaatccct tataaatcaa agaatagac cgagataggg    7260 ttgagtgttg ttccagtttg gaacaagagt ccactattaa agaacgtgga ctccaacgtc    7320
aaagggcgaa aaaccgtcta tcagggcgat ggcccactac gtgaaccatc accctaatca    7380
agttttttgg ggtcgaggtg ccgtaaagca ctaaatcgga acctaaagg gagcccccga    7440 tttagagctt gacggggaaa gccggcgaac gtggcgagaa aggaagggaa gaaagcgaaa    7500
ggagcgggcg ctagggcgct ggcaagtgta gcggtcacgc tgcgcgtaac caccacaccc    7560
gccgcgctta atgcgccgct acagggcgcg tcgcgccatt cgccattcag gctacgcaac    7620
tgttgggaag ggcgatcggt gcgggcctct tcgctattac gccaggctgc a            7671
```

<210> SEQ ID NO 4
<211> LENGTH: 7671
<212> TYPE: DNA
<213> ORGANISM: Artificial Sequence
<220> FEATURE:
<223> OTHER INFORMATION: Synthetic construct (pTR-GPE-human G6PC-S298C)
<220> FEATURE:
<221> NAME/KEY: misc_feature
<222> LOCATION: (17)..(163)
<223> OTHER INFORMATION: Inverted terminal repeat
<220> FEATURE:
<221> NAME/KEY: misc_feature
<222> LOCATION: (182)..(3045)
<223> OTHER INFORMATION: GPE
<220> FEATURE:

```
<221> NAME/KEY: misc_feature
<222> LOCATION: (3051)..(3184)
<223> OTHER INFORMATION: Stuffer sequence
<220> FEATURE:
<221> NAME/KEY: misc_feature
<222> LOCATION: (3185)..(3321)
<223> OTHER INFORMATION: Intron
<220> FEATURE:
<221> NAME/KEY: misc_feature
<222> LOCATION: (3322)..(3367)
<223> OTHER INFORMATION: Stuffer sequence
<220> FEATURE:
<221> NAME/KEY: misc_feature
<222> LOCATION: (3368)..(4441)
<223> OTHER INFORMATION: human G6PC S298C coding sequence
<220> FEATURE:
<221> NAME/KEY: misc_feature
<222> LOCATION: (4259)..(4261)
<223> OTHER INFORMATION: Codon change
<220> FEATURE:
<221> NAME/KEY: misc_feature
<222> LOCATION: (4674)..(4819)
<223> OTHER INFORMATION: Inverted terminal repeat

<400> SEQUENCE: 4
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctagatctg aattcggtac     180 cccctttgaga atccacggtg tctcgatgca gtcagctttc taacaagctg gggcctcacc     240
tgttttccca cggataaaaa cgtgctggag gaagcagaaa ggggctggca ggtggaaaga     300
tgaggaccag ctcatcgtct catgactatg aggttgctct gatccagagg gtccccctgc     360
ctggtggccc accgccagga agactcccac tgtccctgga tgcccagagt gggatgtcaa     420
ctccatcact tatcaactcc ttatccatag gggtattctt cctgaggcgt ctcagaaaac     480
agggccctcc ccatatgctg accacataat agaaccctc ccaactcaga gaccctggct      540
gctagctgcc ctggcatgac ccagacagtg gcctttgtat atgttttttag actcaccttg    600 actcacctct gaccatagaa actctcatcc cagaggtcac tgcaatagtt actccacaac     660
agaggcttat ctgggtagag ggaggctccc tacctatggc ccagcagccc tgacagtgca     720
gatcacatat accccacgcc ccagcactgc ctgccacgca tgggcttact ttacacccac     780
ccacagtcac caacacatta cctgctctcc aaggttaggc gtggcaggag aagtttgctt     840
ggaccagcag aaaccatgca gtcaaggaca actggagtca gcatgggctg ggtgcgagcc     900
cttggtgggg tggggaggag actccaggtc atacctcctg gaggatgttt taatcatttc     960
cagcatggaa tgctgtcaac ttttgccaca gattcattag ctctgagttt cttttttctg    1020
tccccagcta ccccttacat gtcaatatgg acttaatgat gggaaattca ggcaagtttt    1080
taaacatttt attccccctg gctcttatcc tcaaaaaatg catgaatttg gaggcagtgg    1140
ctcatgcctg taatcccaat gctttgctag gttgaggcgg gaggatcact tgaagccagg    1200
aatttgagac cagcctgggc cgcatagtga ccccgtttt ctacaaaaat aaataaataa      1260
ataataaata atagtgatat gaagcatgat taaatagccc tattttttaa aatgcatgag    1320
ttcgttacct gattcattcc ctggttcctt tcacagtcct ccgtgaccca agtgttaggg    1380
ttttggtctc tctactattt gtaggctgat atatagtata cacacacaca cacacacaca    1440
tatacacaca cacagtgtat cttgagcttt cttttgtata tctacacaca tatgtataag    1500
aaagctcaag atatagaagc cctttttcaa aaataactga aagtttcaaa ctctttaagt    1560
ctccagttac catttgtgct gtattcttat ttggaaccat acattcatca tattgttgca    1620
```

```
cagtaagact atacattcat tattttgctt aaacgtatga gttaaaacac ttggccaggc    1680
atggtggttc acacctgtaa tcccagagct ttgggaagcc aagactggca gatctcttga    1740
gctcaggaat tcaagaccag cctgggcaac atggaaaaac cccatctcta caaaagatag    1800
aaaaattagc caggcatggt ggcgtgtgcc tgtggtccca gctactcagg aggctgaggt    1860
gggaggatca cattagccca ggaggttgag gctgcagtga gccgtgatta tgccactgca    1920
ctccagcctg ggagacagag tgagaccctg tttcaaaaaa aagagagaga aaatttaaaa    1980
aagaaaacaa caccaagggc tgtaacttta aggtcattaa atgaattaat cactgcattc    2040
aaaaacgatt actttctggc cctaagagac atgaggccaa taccaggaag ggggttgatc    2100
tcccaaacca gaggcagacc ctagactcta atacagttaa ggaaagacca gcaagatgat    2160
agtccccaat acaatagaag ttactatatt ttatttgttg tttttctttt gttttgtttt    2220
gttttgtttt gttttgtttt agagactggg gtcttgctcg attgcccagg ctgtagtgca    2280
gcggtgggac aatagctcac tgcagactcc aactcctggg ctcaagcaat cctcctgcct    2340
cagcctcctg aatagctggg actacaaggg tacaccatca cacacaccaa acaattttt     2400 taaattttg tgtagaaacg agggtcttgc tttgttgccc aggctggtct ccaactcctg    2460
gcttcaaggg atcctcccac ctcagcctcc caaattgctg ggattacagg tgtgagccac    2520
cacaaccagc cagaacttta ctaattttaa aattaagaac ttaaaacttg aatagctaga    2580
gcaccaagat ttttctttgt ccccaaataa gtgcagttgc aggcatagaa atctgacat     2640 ctttgcaaga atcatcgtgg atgtagactc tgtcctgtgt ctctggcctg gtttcgggga    2700
ccaggagggc agaccettgc actgccaaga agcatgccaa agttaatcat tggccctgct    2760
gagtacatgg ccgatcaggc tgttttttgtg tgcctgtttt tctattttac gtaaatcacc    2820
ctgaacatgt ttgcatcaac ctactggtga tgcacctttg atcaatacat tttagacaaa    2880
cgtggttttt gagtccaaag atcagggctg ggttgacctg aatactggat acagggcata    2940
taaaacaggg gcaaggcaca gactcatagc agagcaatca ccaccaagcc tggaataact    3000
gcaagggctc tgctgacatc ttcctgaggt gccaaggaaa tgaggtctag agaagcttta    3060
ttgcggtagt ttatcacagt taaattgcta acgcagtcag tgcttctgac acaacagtct    3120
cgaacttaag ctgcagtgac tctcttaagg tagccttgca gaagttggtc gtgaggcact    3180
gggcaggtaa gtatcaaggt tacaagacag gtttaaggag accaatagaa actgggcttg    3240
tcgagacaga gaagactctt gcgtttctga taggcaccta ttggtcttac tgacatccac    3300
tttgcctttc tctccacagg tgtccactcc cagttcaatt acagctctta aggccctgca    3360
ggccaccatg gaggaaggaa tgaatgttct ccatgacttt gggatccagt caacacatta    3420
cctccaggtg aattaccaag actcccagga ctggttcatc ttggtgtccg tgatcgcaga    3480
cctcaggaat gccttctacg tcctcttccc catctggttc catcttcagg aagctgtggg    3540
cattaaactc ctttgggtag ctgtgattgg agactggctc aacctcgtct ttaagtggat    3600
tctctttgga cagcgtccat actggtgggt tttggatact gactactaca gcaacacttc    3660
cgtgcccctg ataaagcagt tccctgtaac ctgtgagact ggaccaggga gccctctgg    3720 ccatgccatg ggcacagcag gtgtatacta cgtgatggtc acatctactc tttccatctt    3780
tcagggaaag ataaagccga cctacagatt tcggtgcttg aatgtcattt tgtggttggg    3840
attctgggct gtgcagctga atgtctgtct gtcacgaatc tacctgctg ctcatttttcc     3900 tcatcaagtt gttgctggag tcctgtcagg cattgctgtt gcagaaactt tcagccacat    3960
```

```
ccacagcatc tataatgcca gcctcaagaa atattttctc attaccttct tcctgttcag    4020
cttcgccatc ggattttatc tgctgctcaa gggactgggt gtagacctcc tgtggactct    4080
ggagaaagcc cagaggtggt gcgagcagcc agaatgggtc cacattgaca ccacaccctt    4140
tgccagcctc ctcaagaacc tgggcacgct ctttggcctg gggctggctc tcaactccag    4200
catgtacagg gagagctgca aggggaaact cagcaagtgg ctcccattcc gcctcagctg    4260
cattgtagcc tccctcgtcc tcctgcacgt ctttgactcc ttgaaacccc catcccaagt    4320
cgagctggtc ttctacgtct tgtccttctg caagagtgcg gtagtgcccc tggcatccgt    4380
cagtgtcatc ccctactgcc tcgcccaggt cctgggccag ccgcacaaga agtcgttgta    4440
agcggccgcg gggatccaga catgataaga tacattgatg agtttggaca aaccacaact    4500
agaatgcagt gaaaaaaatg ctttatttgt gaaatttgtg atgctattgc tttatttgta    4560
accattataa gctgcaataa acaagttaac aacaacaatt gcattcattt tatgtttcag    4620 gttcagggg aggtgtggga ggttttttag tcgaccatgc tggggagaga tctaggaacc    4680
cctagtgatg gagttggcca ctccctctct gcgcgctcgc tcgctcactg aggccgcccg    4740
ggcaaagccc gggcgtcggg cgacctttgg tcgcccggcc tcagtgagcg agcgagcgcg    4800
cagagaggga gtggccaacc ccccccccc ccccctgca gccctgcatt aatgaatcgg    4860
ccaacgcgcg gggagaggcg gtttgcgtat gggcgctct ccgcttcct cgctcactga    4920 ctcgctgcgc tcggtcgttc ggctgcggcg agcggtatca gctcactcaa aggcggtaat    4980
acggttatcc acagaatcag gggataacgc aggaaagaac atgtgagcaa aaggccagca    5040
aaaggccagg aaccgtaaaa aggccgcgtt gctggcgttt ttccataggc tccgcccccc    5100
tgacgagcat cacaaaaatc gacgctcaag tcagaggtgg cgaaacccga caggactata    5160
aagataccag gcgtttcccc ctggaagctc cctcgtgcgc tctcctgttc cgaccctgcc    5220
gcttaccgga tacctgtccg cctttctccc ttcgggaagc gtggcgcttt ctcaatgctc    5280
acgctgtagg tatctcagtt cggtgtaggt cgttcgctcc aagctgggct gtgtgcacga    5340 acccccccgtt cagcccgacc gctgcgcctt atccggtaac tatcgtcttg agtccaaccc    5400
ggtaagacac gacttatcgc cactggcagc agccactggt aacaggatta gcagagcgag    5460
gtatgtaggc ggtgctacag agttcttgaa gtggtggcct aactacggct acactagaag    5520
gacagtattt ggtatctgcg ctctgctgaa gccagttacc ttcggaaaaa gagttggtag    5580
ctcttgatcc ggcaaacaaa ccaccgctgg tagcggtggt ttttttgttt gcaagcagca    5640
gattacgcgc agaaaaaaag gatctcaaga agatcctttg atcttttcta cggggtctga    5700
cgctcagtgg aacgaaaact cacgttaagg gattttggtc atgagattat caaaaaggat    5760
cttcacctag atccttttaa attaaaaatg aagttttaaa tcaatctaaa gtatatatga    5820
gtaaacttgg tctgacagtt accaatgctt aatcagtgag gcacctatct cagcgatctg    5880
tctatttcgt tcatccatag ttgcctgact ccccgtcgtg tagataacta cgatacggga    5940
gggcttacca tctggcccca gtgctgcaat gataccgcga cccacgct caccggctcc    6000 agatttatca gcaataaacc agccagccgg aagggccgag cgcagaagtg gtcctgcaac    6060
tttatccgcc tccatccagt ctattaattg ttgccgggaa gctagagtaa gtagttcgcc    6120
agttaatagt ttgcgcaacg ttgttgccat tgctacaggc atcgtggtgt cacgctcgtc    6180
gtttggtatg gcttcattca gctccggttc ccaacgatca aggcgagtta catgatcccc    6240
catgttgtgc aaaaaagcgg ttagctcctt cggtcctccg atcgttgtca gaagtaagtt    6300
ggccgcagtg ttatcactca tggttatggc agcactgcat aattctctta ctgtcatgcc    6360
```

```
atccgtaaga tgcttttctg tgactggtga gtactcaacc aagtcattct gagaatagtg    6420
tatgcggcga ccgagttgct cttgcccggc gtcaatacgg gataataccg cgccacatag    6480
cagaacttta aaagtgctca tcattggaaa acgttcttcg gggcgaaaac tctcaaggat    6540
cttaccgctg ttgagatcca gttcgatgta acccactcgt gcacccaact gatcttcagc    6600
atcttttact ttcaccagcg tttctgggtg agcaaaaaca ggaaggcaaa atgccgcaaa    6660
aaagggaata agggcgacac ggaaatgttg aatactcata ctcttccttt ttcaatatta    6720
ttgaagcatt tatcagggtt attgtctcat gagcggatac atatttgaat gtatttagaa    6780
aaataaacaa ataggggttc cgcgcacatt tccccgaaaa gtgccacctg acgtctaaga    6840
aaccattatt atcatgacat taacctataa aaataggcgt atcacgaggc cctttcgtct    6900
cgcgcgtttc ggtgatgacg gtgaaaacct ctgacacatg cagctcccgg agacggtcac    6960
agcttgtctg taagcggatg ccgggagcag acaagcccgt cagggcgcgt cagcgggtgt    7020
tggcgggtgt cggggctggc ttaactatgc ggcatcagag cagattgtac tgagagtgca    7080
ccatatgcgg tgtgaaatac cgcacagatg cgtaaggaga aaataccgca tcaggaaatt    7140
gtaaacgtta atattttgtt aaaattcgcg ttaaattttt gttaaatcag ctcattttttt    7200 aaccaatagg ccgaaatcgg caaaatccct tataaatcaa agaatagac cgagataggg    7260 ttgagtgttg ttccagtttg gaacaagagt ccactattaa agaacgtgga ctccaacgtc    7320
aaagggcgaa aaccgtcta tcagggcgat ggcccactac gtgaaccatc accctaatca    7380
agttttttgg ggtcgaggtg ccgtaaagca ctaaatcgga acctaaaagg agcccccga    7440 tttagagctt gacggggaaa gccggcgaac gtggcgagaa aggaagggaa gaaagcgaaa    7500
ggagcgggcg ctagggcgct ggcaagtgta gcggtcacgc tgcgcgtaac caccacaccc    7560
gccgcgctta atgcgccgct acagggcgcg tcgcgccatt cgccattcag gctacgcaac    7620
tgttgggaag ggcgatcggt gcgggcctct tcgctattac gccaggctgc a             7671
```

<210> SEQ ID NO 5
<211> LENGTH: 7671
<212> TYPE: DNA
<213> ORGANISM: Artificial Sequence
<220> FEATURE:
<223> OTHER INFORMATION: Synthetic construct (pTR-GPE-co-G6PC-S298C)
<220> FEATURE:
<221> NAME/KEY: misc_feature
<222> LOCATION: (17)..(163)
<223> OTHER INFORMATION: Inverted terminal repeat
<220> FEATURE:
<221> NAME/KEY: misc_feature
<222> LOCATION: (182)..(3045)
<223> OTHER INFORMATION: GPE
<220> FEATURE:
<221> NAME/KEY: misc_feature
<222> LOCATION: (3051)..(3184)
<223> OTHER INFORMATION: Stuffer sequence
<220> FEATURE:
<221> NAME/KEY: misc_feature
<222> LOCATION: (3185)..(3321)
<223> OTHER INFORMATION: Intron
<220> FEATURE:
<221> NAME/KEY: misc_feature
<222> LOCATION: (3322)..(3367)
<223> OTHER INFORMATION: Stuffer sequence
<220> FEATURE:
<221> NAME/KEY: misc_feature
<222> LOCATION: (3368)..(4441)
<223> OTHER INFORMATION: human codon-optimized G6PC coding sequence
<220> FEATURE:
<221> NAME/KEY: misc_feature
<222> LOCATION: (4259)..(4261)

<223> OTHER INFORMATION: Codon change
<220> FEATURE:
<221> NAME/KEY: misc_feature
<222> LOCATION: (4674)..(4819)
<223> OTHER INFORMATION: Inverted terminal repeat

<400> SEQUENCE: 5

```
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actagggtt cctagatctg aattcggtac     180
cccttgaga atccacggtg tctcgatgca gtcagcttc taacaagctg gggcctcacc     240
tgttttccca cggataaaaa cgtgctggag gaagcagaaa ggggctggca ggtggaaaga     300
tgaggaccag ctcatcgtct catgactatg aggttgctct gatccagagg gtccccctgc     360
ctggtggccc accgccagga agactcccac tgtccctgga tgcccagagt gggatgtcaa     420
ctccatcact tatcaactcc ttatccatag gggtattctt cctgaggcgt ctcagaaaac     480
agggccctcc ccatatgctg accacataat agaaccctc ccaactcaga gaccctggct     540
gctagctgcc ctggcatgac ccagacagtg gcctttgtat atgttttag actcaccttg     600
actcacctct gaccatagaa actctcatcc cagaggtcac tgcaatagtt actccacaac     660
agaggcttat ctgggtagag ggaggctccc tacctatggc ccagcagccc tgacagtgca     720
gatcacatat accccacgcc ccagcactgc ctgccacgca tgggcttact ttacacccac     780
ccacagtcac caacacatta cctgctctcc aaggttaggc gtggcaggag aagtttgctt     840
ggaccagcag aaaccatgca gtcaaggaca actggagtca gcatgggctg ggtgcgagcc     900
cttggtgggg tggggaggag actccaggtc atacctcctg gaggatgttt taatcatttc     960
cagcatggaa tgctgtcaac ttttgccaca gattcattag ctctgagttt cttttttctg    1020
tccccagcta cccttacat gtcaatatgg acttaatgat gggaaattca ggcaagtttt    1080
taaacatttt attcccctg gctcttatcc tcaaaaaatg catgaatttg gaggcagtgg    1140
ctcatgcctg taatcccaat gctttgctag gttgaggcgg gaggatcact tgaagccagg    1200
aatttgagac cagcctgggc cgcatagtga caccccgtt ctacaaaaat aaataaataa    1260
ataataaata atagtgatat gaagcatgat taaatagccc tattttttaa aatgcatgag    1320
ttcgttacct gattcattcc ctggttcctt tcacagtcct ccgtgaccca agtgttaggg    1380
ttttggtctc tctactattt gtaggctgat atatagtata cacacacaca cacacacaca    1440
tatacacaca cacagtgtat cttgagcttt cttttgtata tctacacaca tatgtataag    1500
aaagctcaag atatagaagc ccttttcaa aaataactga agtttcaaa ctctttaagt    1560
ctccagttac cattttgctg gtattcttat ttggaaccat acattcatca tattgttgca    1620
cagtaagact atacattcat tattttgctt aaacgtatga gttaaaacac ttggccaggc    1680
atggtggttc acacctgtaa tcccagagct tgggaagcc aagactggca gatctcttga    1740
gctcaggaat tcaagaccag cctgggcaac atggaaaaac cccatctcta caaaagatag    1800
aaaaattagc caggcatggt ggcgtgtgcc tgtggtccca gctactcagg aggctgaggt    1860
gggaggatca cattagccca ggaggttgag gctgcagtga gccgtgatta tgccactgca    1920
ctccagcctg ggagacagag tgagaccctg tttcaaaaaa aagagagaga aaatttaaaa    1980
aagaaaacaa caccaagggc tgtaacttta aggtcattaa atgaattaat cactgcattc    2040
aaaaacgatt actttctggc cctaagagac atgaggccaa taccaggaag ggggttgatc    2100
tcccaaacca gaggcagacc ctagactcta atacagttaa ggaaagacca gcaagatgat    2160
```

-continued

```
agtccccaat acaatagaag ttactatatt ttatttgttg tttttctttt gttttgtttt    2220
gttttgtttt gttttgtttt gttttgtttt agagactggg gtcttgctcg attgcccagg ctgtagtgca    2280
gcggtgggac aatagctcac tgcagactcc aactcctggg ctcaagcaat cctcctgcct    2340
cagcctcctg aatagctggg actacaaggg tacaccatca cacaccaa aacaattttt    2400
taaattttg tgtagaaacg agggtcttgc tttgttgccc aggctggtct ccaactcctg    2460
gcttcaaggg atcctcccac ctcagcctcc caaattgctg ggattacagg tgtgagccac    2520
cacaaccagc cagaacttta ctaattttaa aattaagaac ttaaaacttg aatagctaga    2580
gcaccaagat ttttctttgt ccccaaataa gtgcagttgc aggcatagaa aatctgacat    2640
ctttgcaaga atcatcgtgg atgtagactc tgtcctgtgt ctctggcctg gtttcgggga    2700
ccaggagggc agacccttgc actgccaaga agcatgccaa agttaatcat tggccctgct    2760
gagtacatgg ccgatcaggc tgtttttgtg tgcctgtttt tctatttac gtaaatcacc    2820
ctgaacatgt ttgcatcaac ctactggtga tgcacctttg atcaatacat tttagacaaa    2880
cgtggttttt gagtccaaag atcagggctg ggttgacctg aatactggat acagggcata    2940
taaaacaggg gcaaggcaca gactcatagc agagcaatca ccaccaagcc tggaataact    3000
gcaagggctc tgctgacatc ttcctgaggt gccaaggaaa tgaggtctag agaagcttta    3060
ttgcggtagt ttatcacagt taaattgcta acgcagtcag tgcttctgac acaacagtct    3120
cgaacttaag ctgcagtgac tctcttaagg tagccttgca gaagttggtc gtgaggcact    3180
gggcaggtaa gtatcaaggt tacaagacag gtttaaggag accaatagaa actgggcttg    3240
tcgagacaga gaagactctt gcgtttctga taggcaccta ttggtcttac tgacatccac    3300
tttgcctttc tctccacagg tgtccactcc cagttcaatt acagctctta aggccctgca    3360
ggccaccatg aagagggca tgaacgtgct gcacgacttc ggcatccaga gcacccacta    3420
tctgcaggtc aactaccagg acagccagga ctggttcatc ctggtgtccg tgatcgccga    3480
cctgcggaac gccttctacg tgctgttccc catctggttc catctgcaag aagccgtcgg    3540
catcaagctg ctgtgggtgg ccgtgatcgg cgattggctg aacctggtgt tcaagtggat    3600
cctgttcggc cagcggccct attggtgggt gctggacacc gactactaca gcaacaccag    3660
cgtgccctg atcaagcagt tccccgtgac ctgcgagaca ggccctggct ctccttctgg    3720
ccacgccatg ggaacagccg gcgtgtacta cgtgatggtc accagcaccc tgagcatctt    3780
ccagggcaag atcaagccca cctaccggtt ccggtgcctg aacgtgatcc tgtggctggg    3840
cttctgggcc gtgcagctga acgtgtgcct gagccggatc tacctggccg cccacttccc    3900
acatcaagtg gtggccggcg tgctgagcgg aatcgccgtg gccgagacat tcagccacat    3960
ccacagcatc tacaacgcca gcctgaagaa gtacttcctg atcacattct ttctgttcag    4020
cttcgccatc ggcttctacc tgctgctgaa gggcctgggc gtggacctgc tgtggaccct    4080
ggaaaaggcc cagcggtggt gcgagcagcc cgagtgggtg cacatcgaca ccacccctt    4140
cgccagcctg ctgaagaacc tgggcaccct gtttggactg gcctggccc tgaacagcag    4200
catgtacaga gagagctgca agggcaagct gagcaagtgg ctgcccttcc ggctgagctg    4260
catcgtggcc agcctggtgc tgctgcacgt gttcgacagc ctgaagcccc ccagccaggt    4320
ggaactggtg ttttacgtgc tgagcttctg caagagcgcc gtggtgcccc tggcctccgt    4380
gtctgtgatc ccctactgcc tggctcaggt gctgggccag cccacaaga agtccctctg    4440
agcggccgcg gggatccaga catgataaga tacattgatg agtttggaca aaccacaact    4500
```

```
agaatgcagt gaaaaaaatg ctttatttgt gaaatttgtg atgctattgc tttatttgta    4560
accattataa gctgcaataa acaagttaac aacaacaatt gcattcattt tatgtttcag    4620
gttcaggggg aggtgtggga ggttttttag tcgaccatgc tggggagaga tctaggaacc    4680
cctagtgatg gagttggcca ctccctctct gcgcgctcgc tcgctcactg aggccgcccg    4740
ggcaaagccc gggcgtcggg cgacctttgg tcgcccggcc tcagtgagcg agcgagcgcg    4800
cagagaggga gtggccaacc cccccccccc cccccctgca gccctgcatt aatgaatcgg    4860
ccaacgcgcg gggagaggcg gtttgcgtat tgggcgctct ccgcttcct cgctcactga    4920 ctcgctgcgc tcggtcgttc ggctgcggcg agcggtatca gctcactcaa aggcggtaat    4980
acggttatcc acagaatcag gggataacgc aggaaagaac atgtgagcaa aaggccagca    5040
aaaggccagg aaccgtaaaa aggccgcgtt gctggcgttt ttccataggc tccgcccccc    5100
tgacgagcat cacaaaaatc gacgctcaag tcagaggtgg cgaaacccga caggactata    5160
aagataccag gcgtttcccc ctggaagctc cctcgtgcgc tctcctgttc cgaccctgcc    5220
gcttaccgga tacctgtccg cctttctccc ttcgggaagc gtggcgcttt ctcaatgctc    5280
acgctgtagg tatctcagtt cggtgtaggt cgttcgctcc aagctgggct gtgtgcacga    5340
accccccgtt cagcccgacc gctgcgcctt atccggtaac tatcgtcttg agtccaaccc    5400
ggtaagacac gacttatcgc cactggcagc agccactggt aacaggatta gcagagcgag    5460
gtatgtaggc ggtgctacag agttcttgaa gtggtggcct aactacggct acactagaag    5520
gacagtattt ggtatctgcg ctctgctgaa gccagttacc ttcggaaaaa gagttggtag    5580
ctcttgatcc ggcaaacaaa ccaccgctgg tagcggtggt ttttttgttt gcaagcagca    5640
gattacgcgc agaaaaaaag gatctcaaga agatcctttg atcttttcta cggggtctga    5700
cgctcagtgg aacgaaaact cacgttaagg gattttggtc atgagattat caaaaaggat    5760
cttcacctag atccttttaa attaaaaatg aagttttaaa tcaatctaaa gtatatatga    5820
gtaaacttgg tctgacagtt accaatgctt aatcagtgag gcacctatct cagcgatctg    5880
tctatttcgt tcatccatag ttgcctgact ccccgtcgtg tagataacta cgatacggga    5940
gggcttacca tctggcccca gtgctgcaat gataccgcga gacccacgct caccggctcc    6000
agatttatca gcaataaacc agccagccgg aagggccgag cgcagaagtg gtcctgcaac    6060
tttatccgcc tccatccagt ctattaattg ttgccgggaa gctagagtaa gtagttcgcc    6120
agttaatagt ttgcgcaacg ttgttgccat tgctacaggc atcgtggtgt cacgctcgtc    6180
gtttggtatg gcttcattca gctccggttc ccaacgatca aggcgagtta catgatcccc    6240
catgttgtgc aaaaaagcgg ttagctcctt cggtcctccg atcgttgtca gaagtaagtt    6300
ggccgcagtg ttatcactca tggttatggc agcactgcat aattctctta ctgtcatgcc    6360
atccgtaaga tgcttttctg tgactggtga gtactcaacc aagtcattct gagaatagtg    6420
tatgcggcga ccgagttgct cttgcccggc gtcaatacgg gataataccg cgccacatag    6480
cagaacttta aaagtgctca tcattggaaa acgttcttcg ggcgaaaac tctcaaggat    6540 cttaccgctg ttgagatcca gttcgatgta acccactcgt gcacccaact gatcttcagc    6600
atcttttact ttcaccagcg tttctgggtg agcaaaaaca ggaaggcaaa atgccgcaaa    6660
aaagggaata agggcgacac ggaaatgttg aatactcata ctcttccttt ttcaatatta    6720
ttgaagcatt tatcagggtt attgtctcat gagcggatac atatttgaat gtatttagaa    6780
aaataaacaa ataggggttc cgcgcacatt tccccgaaaa gtgccacctg acgtctaaga    6840
aaccattatt atcatgacat taacctataa aaataggcgt atcacgaggc cctttcgtct    6900
```

-continued

```
cgcgcgtttc ggtgatgacg gtgaaaacct ctgacacatg cagctcccgg agacggtcac      6960
agcttgtctg taagcggatg ccgggagcag acaagcccgt cagggcgcgt cagcgggtgt      7020
tggcgggtgt cggggctggc ttaactatgc ggcatcagag cagattgtac tgagagtgca      7080
ccatatgcgg tgtgaaatac cgcacagatg cgtaaggaga aaataccgca tcaggaaatt      7140
gtaaacgtta atattttgtt aaaattcgcg ttaaattttt gttaaatcag ctcatttttt      7200
aaccaatagg ccgaaatcgg caaaatccct tataaatcaa agaatagac cgagataggg       7260 ttgagtgttg ttccagtttg gaacaagagt ccactattaa agaacgtgga ctccaacgtc      7320
aaagggcgaa aaaccgtcta tcagggcgat ggcccactac gtgaaccatc accctaatca     7380
agttttttgg ggtcgaggtg ccgtaaagca ctaaatcgga accctaaagg gagcccccga      7440
tttagagctt gacggggaaa gccggcgaac gtggcgagaa aggaagggaa gaaagcgaaa      7500
ggagcgggcg ctagggcgct ggcaagtgta gcggtcacgc tgcgcgtaac caccacaccc     7560
gccgcgctta atgcgccgct acagggcgcg tcgcgccatt cgccattcag gctacgcaac     7620
tgttgggaag ggcgatcggt gcgggcctct tcgctattac gccaggctgc a              7671
```

<210> SEQ ID NO 6
<211> LENGTH: 1074
<212> TYPE: DNA
<213> ORGANISM: Artificial Sequence
<220> FEATURE:
<223> OTHER INFORMATION: Synthetic polynucleotide

<400> SEQUENCE: 6

```
atggaggaag gaatgaatgt tctccatgac tttgggatcc agtcaacaca ttacctccag       60
gtgaattacc aagactccca ggactggttc atcttggtgt ccgtgatcgc agacctcagg      120
aatgccttct acgtcctctt ccccatctgg ttccatcttc aggaagctgt gggcattaaa      180
ctcctttggg tagctgtgat tggagactgg ctcaacctcg tctttaagtg gattctcttt      240
ggacagcgtc catactggtg ggttttggat actgactact acagcaacac ttccgtgccc      300
ctgataaagc agttccctgt aacctgtgag actggaccag ggagcccctc tggccatgcc      360
atgggcacag caggtgtata ctacgtgatg gtcacatcta ctctttccat ctttcaggga      420
aagataaagc cgacctacag atttcggtgc ttgaatgtca ttttgtggtt gggattctgg      480
gctgtgcagc tgaatgtctg tctgtcacga atctaccttg ctgctcattt tcctcatcaa      540
gttgttgctg gagtcctgtc aggcattgct gttgcagaaa ctttcagcca catccacagc      600
atctataatc ccagcctcaa gaatatttt ctcattacct tcttcctgtt cagcttcgcc      660
atcggatttt atctgctgct caagggactg ggtgtagacc tcctgtggac tctggagaaa      720
gcccagaggt ggtgcgagca gccagaatgg gtccacattg acaccacacc ctttgccagc      780
ctcctcaaga acctgggcac gctctttggc ctggggctgg ctctcaactc cagcatgtac      840
agggagagct gcaaggggaa actcagcaag tggctcccat tccgcctcag ctgcattgta      900
gcctccctcg tcctcctgca cgtctttgac tccttgaaac cccatcccca gtcgagctg      960 gtcttctacg tcttgtcctt ctgcaagagt gcggtagtgc ccctggcatc cgtcagtgtc      1020 atccccact gcctcgccca ggtcctgggc cagccgcaca gaagtcgtt gtaa             1074
```

<210> SEQ ID NO 7
<211> LENGTH: 1074
<212> TYPE: DNA
<213> ORGANISM: Artificial Sequence
<220> FEATURE:

<223> OTHER INFORMATION: Synthetic polynucleotide

<400> SEQUENCE: 7

```
atggaagagg gcatgaacgt gctgcacgac ttcggcatcc agagcaccca ctatctgcag      60
gtcaactacc aggacagcca ggactggttc atcctggtgt ccgtgatcgc cgacctgcgg     120
aacgccttct acgtgctgtt ccccatctgg ttccatctgc aagaagccgt cggcatcaag     180
ctgctgtggg tggccgtgat cggcgattgg ctgaacctgg tgttcaagtg gatcctgttc     240
ggccagcggc cctattggtg ggtgctggac accgactact acagcaacac cagcgtgccc     300
ctgatcaagc agttccccgt gacctgcgag acaggccctg gctctccttc tggccacgcc     360
atgggaacag ccggcgtgta ctacgtgatg gtcaccagca ccctgagcat cttccagggc     420
aagatcaagc ccacctaccg gttccggtgc ctgaacgtga tcctgtggct gggcttctgg     480
gccgtgcagc tgaacgtgtg cctgagccgg atctacctgg ccgcccactt ccacatcaa     540
gtggtggccg gcgtgctgag cggaatcgcc gtggccgaga cattcagcca catccacagc     600
atctacaacg ccagcctgaa gaagtacttc ctgatcacat tctttctgtt cagcttcgcc     660
atcggcttct acctgctgct gaagggcctg ggcgtggacc tgctgtggac cctggaaaag     720
gcccagcggt ggtgcgagca gcccgagtgg gtgcacatcg acaccacccc cttcgccagc     780
ctgctgaaga acctgggcac cctgtttgga ctgggcctgg ccctgaacag cagcatgtac     840
agagagagct gcaagggcaa gctgagcaag tggctgccct ccggctgag ctgcatcgtg      900
gccagcctgg tgctgctgca cgtgttcgac agcctgaagc ccccagcca ggtggaactg      960
gtgttttacg tgctgagctt ctgcaagagc gccgtggtgc ccctggcctc cgtgtctgtg    1020
atcccctact gcctggctca ggtgctgggc cagccccaca gaagtccct ctga          1074
```

<210> SEQ ID NO 8
<211> LENGTH: 357
<212> TYPE: PRT
<213> ORGANISM: Artificial Sequence
<220> FEATURE:
<223> OTHER INFORMATION: Synthetic polypeptide

<400> SEQUENCE: 8

```
Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160
```

```
Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Cys Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355

<210> SEQ ID NO 9
<211> LENGTH: 357
<212> TYPE: PRT
<213> ORGANISM: Artificial Sequence
<220> FEATURE:
<223> OTHER INFORMATION: Synthetic polypeptide

<400> SEQUENCE: 9

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160
```

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Cys Ile Val Val Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355

<210> SEQ ID NO 10
<211> LENGTH: 357
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Xaa = Lys or Glu
<220> FEATURE:
<221> NAME/KEY: MISC_FEATURE
<222> LOCATION: (54)..(54)
<223> OTHER INFORMATION: Xaa = Arg or Gln
<220> FEATURE:
<221> NAME/KEY: MISC_FEATURE
<222> LOCATION: (139)..(139)
<223> OTHER INFORMATION: Xaa = Arg or Gln
<220> FEATURE:
<221> NAME/KEY: MISC_FEATURE
<222> LOCATION: (142)..(142)
<223> OTHER INFORMATION: Xaa = Lys or Ile
<220> FEATURE:
<221> NAME/KEY: MISC_FEATURE
<222> LOCATION: (196)..(196)
<223> OTHER INFORMATION: Xaa = Arg or Ser
<220> FEATURE:
<221> NAME/KEY: MISC_FEATURE
<222> LOCATION: (199)..(199)
<223> OTHER INFORMATION: Xaa = Gln or His
<220> FEATURE:
<221> NAME/KEY: MISC_FEATURE
<222> LOCATION: (242)..(242)
<223> OTHER INFORMATION: Xaa = Arg or Gln
<220> FEATURE:
<221> NAME/KEY: MISC_FEATURE
<222> LOCATION: (247)..(247)
<223> OTHER INFORMATION: Xaa = Arg or Gln

```
<220> FEATURE:
<221> NAME/KEY: MISC_FEATURE
<222> LOCATION: (292)..(292)
<223> OTHER INFORMATION: Xaa = Phe or Leu
<220> FEATURE:
<221> NAME/KEY: MISC_FEATURE
<222> LOCATION: (298)..(298)
<223> OTHER INFORMATION: Xaa = Cys or Ser
<220> FEATURE:
<221> NAME/KEY: MISC_FEATURE
<222> LOCATION: (301)..(301)
<223> OTHER INFORMATION: Xaa = Val or Ala
<220> FEATURE:
<221> NAME/KEY: MISC_FEATURE
<222> LOCATION: (318)..(318)
<223> OTHER INFORMATION: Xaa = Thr or Val
<220> FEATURE:
<221> NAME/KEY: MISC_FEATURE
<222> LOCATION: (324)..(324)
<223> OTHER INFORMATION: Xaa = Thr or Val
<220> FEATURE:
<221> NAME/KEY: MISC_FEATURE
<222> LOCATION: (332)..(332)
<223> OTHER INFORMATION: Xaa = Ala or Val
<220> FEATURE:
<221> NAME/KEY: MISC_FEATURE
<222> LOCATION: (347)..(347)
<223> OTHER INFORMATION: Xaa = Arg or Gln
<220> FEATURE:
<221> NAME/KEY: MISC_FEATURE
<222> LOCATION: (349)..(349)
<223> OTHER INFORMATION: Xaa = Phe or Leu
<220> FEATURE:
<221> NAME/KEY: MISC_FEATURE
<222> LOCATION: (350)..(350)
<223> OTHER INFORMATION: Xaa = Asp or Gly
<220> FEATURE:
<221> NAME/KEY: MISC_FEATURE
<222> LOCATION: (353)..(353)
<223> OTHER INFORMATION: Xaa = Asp or His

<400> SEQUENCE: 10

Met Glu Xaa Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Xaa Glu Ala Val Gly Ile Lys Leu Leu Trp Val
50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
            85                  90                  95

Thr Ser Val Pro Leu Ile Lys Gln Phe Pro Val Thr Cys Glu Thr Gly
        100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Xaa Gly Lys Xaa Lys Pro
130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
            165                 170                 175

Phe Pro His Gln Val Val Ala Gly Val Leu Ser Gly Ile Ala Val Ala
        180                 185                 190
```

```
Glu Thr Phe Xaa His Ile Xaa Ser Ile Tyr Asn Ala Ser Leu Lys Lys
            195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Xaa Arg Trp Cys Glu Xaa Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Xaa Pro Phe Arg Leu Ser Xaa Ile Val Xaa Ser Leu Val
290                 295                 300

Leu Leu His Val Phe Asp Ser Leu Lys Pro Pro Ser Gln Xaa Glu Leu
305                 310                 315                 320

Val Phe Tyr Xaa Leu Ser Phe Cys Lys Ser Ala Xaa Val Pro Leu Ala
                325                 330                 335

Ser Val Ser Val Ile Pro Tyr Cys Leu Ala Xaa Val Xaa Xaa Gln Pro
            340                 345                 350

Xaa Lys Lys Ser Leu
        355

<210> SEQ ID NO 11
<211> LENGTH: 1074
<212> TYPE: DNA
<213> ORGANISM: Homo sapiens

<400> SEQUENCE: 11
atggaggaag gaatgaatgt tctccatgac tttgggatcc agtcaacaca ttacctccag      60
gtgaattacc aagactccca ggactggttc atcttggtgt ccgtgatcgc agacctcagg     120
aatgccttct acgtcctctt ccccatctgg ttccatcttc aggaagctgt gggcattaaa     180
ctcctttggg tagctgtgat tggagactgg ctcaacctcg tctttaagtg gattctcttt     240
ggacagcgtc catactggtg ggttttggat actgactact acagcaacac ttccgtgccc     300
ctgataaagc agttccctgt aacctgtgag actggaccag ggagcccctc tggccatgcc     360
atgggcacag caggtgtata ctacgtgatg gtcacatcta ctctttccat ctttcaggga     420
aagataaagc cgacctacag atttcggtgc ttgaatgtca ttttgtggtt gggattctgg     480
gctgtgcagc tgaatgtctg tctgtcacga atctaccttg ctgctcattt cctcatcaa      540 gttgttgctg gagtcctgtc aggcattgct gttgcagaaa ctttcagcca catccacagc     600
atctataatg ccagcctcaa gaaatatttt ctcattacct tcttcctgtt cagcttcgcc     660
atcggatttt atctgctgct caagggactg gtgtagacc tcctgtggac tctggagaaa      720
gcccagaggt ggtgcgagca gccagaatgg gtccacattg acaccacacc ctttgccagc     780
ctcctcaaga acctgggcac gctctttggc ctggggctgg ctctcaactc agcatgtac      840 agggagagct gcaaggggaa actcagcaag tggctcccat tccgcctcag ctctattgta     900
gcctccctcg tcctcctgca cgtctttgac tccttgaaac ccccatccca agtcgagctg     960
gtcttctacg tcttgtcctt ctgcaagagt gcggtagtgc ccctggcatc cgtcagtgtc    1020
atcccctact gcctcgccca ggtcctgggc cagccgcaca agaagtcgtt gtaa          1074
```